(12) United States Patent
Wendel et al.

(10) Patent No.: US 9,241,941 B2
(45) Date of Patent: Jan. 26, 2016

(54) METHODS FOR TREATMENT OF LYMPHOMAS WITH MUTATIONS IN CELL CYCLE GENES

(71) Applicant: Memorial Sloan-Kettering Cancer Center, New York, NY (US)

(72) Inventors: Hans Guido Wendel, New York, NY (US); Elisa Oricchio, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 103 days.

(21) Appl. No.: 13/826,056

(22) Filed: Mar. 14, 2013

(65) Prior Publication Data

US 2014/0080838 A1    Mar. 20, 2014

Related U.S. Application Data

(60) Provisional application No. 61/744,174, filed on Sep. 20, 2012, provisional application No. 61/796,120, filed on Nov. 2, 2012.

(51) Int. Cl.
| | | |
|---|---|---|
| *A61K 31/519* | (2006.01) | |
| *A61K 31/495* | (2006.01) | |
| *G01N 33/68* | (2006.01) | |
| *C12Q 1/68* | (2006.01) | |
| *A61K 45/06* | (2006.01) | |
| *A61K 31/404* | (2006.01) | |
| *A61K 31/635* | (2006.01) | |
| *G01N 33/574* | (2006.01) | |

(52) U.S. Cl.
CPC ............. *A61K 31/519* (2013.01); *A61K 31/404* (2013.01); *A61K 31/495* (2013.01); *A61K 31/635* (2013.01); *A61K 45/06* (2013.01); *C12Q 1/6886* (2013.01); *G01N 33/57407* (2013.01); *G01N 33/6893* (2013.01); *C12Q 2600/158* (2013.01)

(58) Field of Classification Search
USPC .............................. 514/252.1, 252.12, 252.16
See application file for complete search history.

(56) References Cited

U.S. PATENT DOCUMENTS

2008/0214521 A1*  9/2008  Schuler .................... 514/211.08
2010/0227838 A1*  9/2010  Shah et al. ...................... 514/89

OTHER PUBLICATIONS

Fry et al. (Mol Cancer Ther, 2004, 3(11): 1427-1437).*
Wiesenthal, (Human Tumor Assay Journal, on-line at http://weisenthal.org/synergy1.htm, Mar. 14, 2012).*
Berenbaum (Clin exp Immunol, 1997, 28:1-18).*
Burnette, W. Neal. ""Western blotting": electrophoretic transfer of proteins from sodium dodecyl sulfate-polyacrylamide gels to unmodified nitrocellulose and radiographic detection with antibody and radioiodinated protein A." Analytical biochemistry 112.2 (1981): 195-203.
Ciriello, Giovanni, et al. "Mutual exclusivity analysis identifies oncogenic network modules." Genome research 22.2 (2012): 398-406.
Egle, Alexander, et al. "VavP-Bcl2 transgenic mice develop follicular lymphoma preceded by germinal center hyperplasia." Blood 103.6 (2004): 2276-2283.
Federico, M. M. "FLIPI-2 predicts for outcomes after active therapy." J Clin Oncol 27 (2009): 4555-62.
Filippakopoulos, Panagis, et al. "Selective inhibition of BET bromodomains." Nature 468.7327 (2010): 1067-1073.
Flaherty, Keith T., et al. "Phase I, dose-escalation trial of the oral cyclin-dependent kinase 4/6 inhibitor PD 0332991, administered using a 21-day schedule in patients with advanced cancer." Clinical Cancer Research 18.2 (2012): 568-576.
Fry et al. (Mol Cancer Ther, 2004,3(11): 1427-1437).
Grønbæk, K., et al. "Concurrent disruption of p16INK4a and the ARF-p53 pathway predicts poor prognosis in aggressive non-Hodgkin's lymphoma." Leukemia 14.1727 (2000): 35.
Hans, Christine P., et al. "A significant diffuse component predicts for inferior survival in grade 3 follicular lymphoma, but cytologic subtypes do not predict survival." Blood 101.6 (2003): 2363-2367.
Eric D., et al. "A clinicopathologic evaluation of follicular lymphoma grade 3A versus grade 3B reveals no survival differences." Archives of pathology & laboratory medicine 128.8 (2004): 863-868.
Jardin, Fabrice, et al. "Diffuse large B-cell lymphomas with CDKN2A deletion have a distinct gene expression signature and a poor prognosis under R-CHOP treatment: a GELA study." Blood 116.7 (2010): 1092-1104.
Lenz, Georg, et al. "Molecular subtypes of diffuse large B-cell lymphoma arise by distinct genetic pathways." Proceedings of the National Academy of Sciences 105.36 (2008): 13520-13525.
Lowe, Scott W., Enrique Cepero, and Gerard Evan. "Intrinsic tumour suppression." Nature 432.7015 (2004): 307-315.
Martin, Anita R., et al. "Prognostic value of cellular proliferation and histologic grade in follicular lymphoma." Blood 85.12 (1995): 3671-3678.

(Continued)

*Primary Examiner* — Yan Xiao
(74) *Attorney, Agent, or Firm* — Mark S. Cohen; Pearl Cohen Zedek Latzer Baratz LLP

(57) ABSTRACT

The present disclosure identifies a novel subtype of follicular lymphoma (FL) characterized by dysregulation of the cyclin/CDK/RB proliferative pathway. This subtype of FL is associated with increased malignancy and mortality, relative to FL which is not associated with cell cycle dysregulation. Accordingly, this disclosure presents novel methods to subtype FL and stratify patient risk by detection of biomarkers associated with RB inactivation. This disclosure further presents novel therapies for the treatment of FL subtyped by inactivation of RB.

10 Claims, 11 Drawing Sheets

Figure 1:
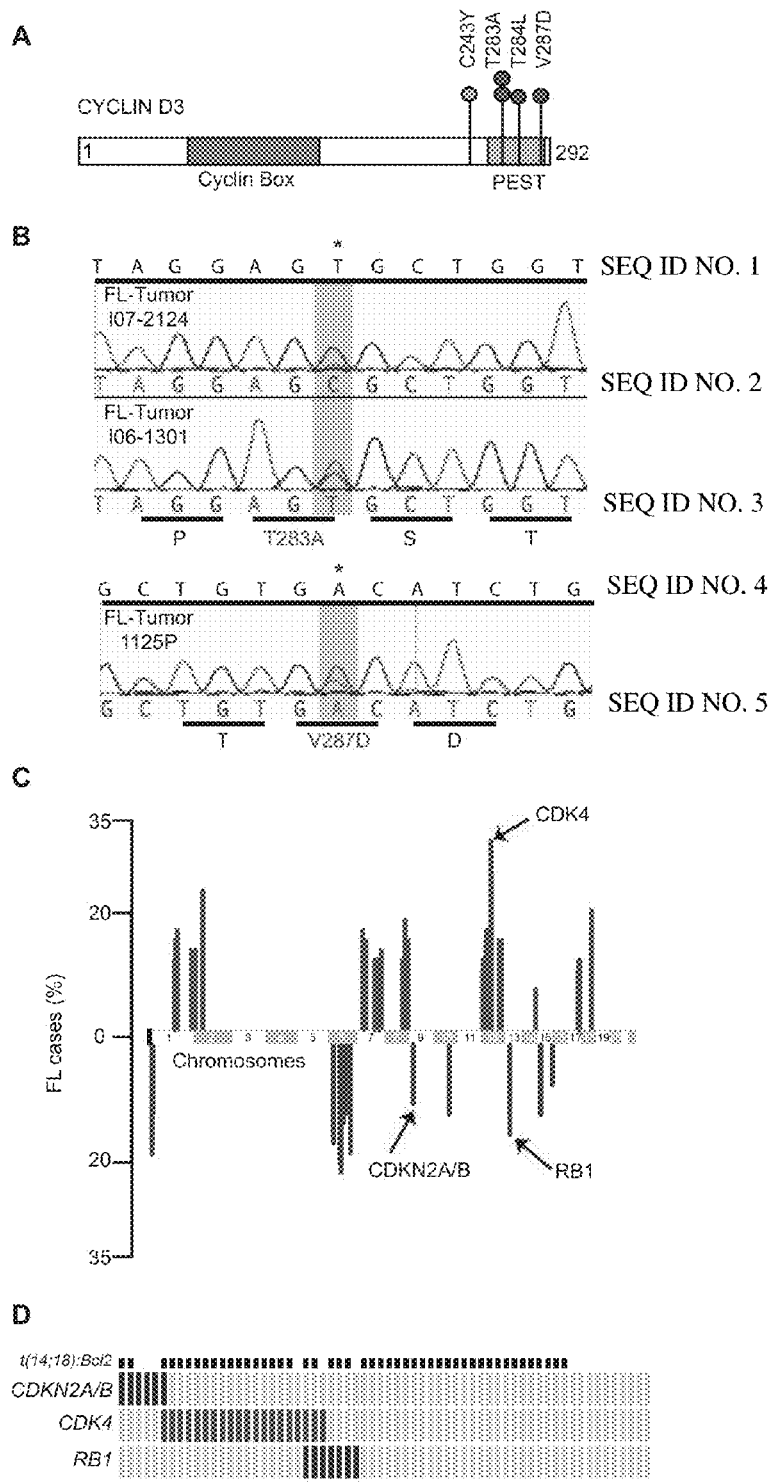

(10 of 11 Drawing Sheet(s) Filed in Color)

(56) References Cited

OTHER PUBLICATIONS

Monti, Stefano, et al. "Integrative analysis reveals an outcome-associated and targetable pattern of p53 and cell cycle deregulation in diffuse large B cell lymphoma." Cancer cell 22.3 (2012): 359-372.

Morin, Ryan D., et al. "Frequent mutation of histone-modifying genes in non-Hodgkin lymphoma." Nature 476.7360 (2011): 298-303.

Musgrove, Elizabeth A., et al. "Cyclin D as a therapeutic target in cancer." Nature Reviews Cancer 11.8 (2011): 558-572.

Naderi, Soheil, et al. "cAMP-induced degradation of cyclin D3 through association with GSK-3β." Journal of cell science 117.17 (2004): 3769-3783.

Oltersdorf, Tilman, et al. "An inhibitor of Bcl-2 family proteins induces regression of solid tumours." Nature 435.7042 (2005): 677-681.

Oricchio, Elisa, et al. "The Eph-receptor A7 is a soluble tumor suppressor for follicular lymphoma." Cell 147.3 (2011): 554-564.

Pasqualucci, Laura, et al. "Analysis of the coding genome of diffuse large B-cell lymphoma." Nature genetics 43.9 (2011): 830-837.

Pruneri, Giancarlo, et al. "Cyclin D3 immunoreactivity in follicular lymphoma is independent of the t (6; 14)(p21.1; q32.3) translocation or cyclin D3 gene amplification and is correlated with histologic grade and Ki-67 labeling index." International journal of cancer 112.1 (2004): 71-77.

Schatz, Jonathan H., et al. "Targeting cap-dependent translation blocks converging survival signals by AKT and PIM kinases in lymphoma." The Journal of experimental medicine 208.9 (2011): 1799-1807.

Schmitz, Roland, et al. "Burkitt lymphoma pathogenesis and therapeutic targets from structural and functional genomics." Nature 490.7418 (2012): 116-120.

Solal-Céligny, Philippe, et al. "Follicular lymphoma international prognostic index." Blood 104.5 (2004): 1258-1265.

Steidl, Christian, et al. "MHC class II transactivator CIITA is a recurrent gene fusion partner in lymphoid cancers." Nature 471.7338 (2011): 377-381.

Wilson, Wyndham H., et al. "Navitoclax, a targeted high-affinity inhibitor of BCL-2, in lymphoid malignancies: a phase 1 dose-escalation study of safety, pharmacokinetics, pharmacodynamics, and antitumour activity." The lancet oncology 11.12 (2010): 1149-1159.

* cited by examiner

SEQUENCE LISTING

```
<160> NUMBER OF SEQ ID NOS: 5

<210> SEQ ID NO 1
<211> LENGTH: 13
<212> TYPE: DNA
<213> ORGANISM: Homo sapiens

<400> SEQUENCE: 1
taggagtgct ggt                                                        13

<210> SEQ ID NO 2
<211> LENGTH: 13
<212> TYPE: DNA
<213> ORGANISM: Homo sapiens

<400> SEQUENCE: 2
taggagcgct ggt                                                        13

<210> SEQ ID NO 3
<211> LENGTH: 13
<212> TYPE: DNA
<213> ORGANISM: Homo sapiens

<400> SEQUENCE: 3
taggagtgct ggt                                                        13

<210> SEQ ID NO 4
<211> LENGTH: 13
<212> TYPE: DNA
<213> ORGANISM: Homo sapiens

<400> SEQUENCE: 4
gctgtgacat ctg                                                        13

<210> SEQ ID NO 5
<211> LENGTH: 13
<212> TYPE: DNA
<213> ORGANISM: Homo sapiens

<400> SEQUENCE: 5
gctgtgacat ctg                                                        13
```

METHODS FOR TREATMENT OF LYMPHOMAS WITH MUTATIONS IN CELL CYCLE GENES

CROSS-REFERENCE TO RELATED APPLICATIONS

This application claims priority to U.S. provisional application 61/744,174, filed Sep. 20, 2012, and U.S. provisional application 61/796,120, filed Nov. 2, 2012, each of which is incorporated herein in its entirety.

STATEMENT REGARDING FEDERALLY SPONSORED RESEARCH OR DEVELOPMENT

This invention was made with government support under Grant No. R01-CA142798-01 awarded by the U.S. National Institutes of Health/National Cancer Institute. The government has certain rights in the invention.

INCORPORATION BY REFERENCE OF SEQUENCE LISTING

The Sequence Listing in the ASCII text file, named as 29766_SEQ.txt, of 1 KB, created on Jul. 24, 2013, and submitted to the United States Patent and Trademark Office via EFS-Web, is incorporated herein by reference.

BACKGROUND OF THE DISCLOSURE

Lymphomas are cancerous growths of lymph node cells.

Follicular lymphoma (FL) is a form of lymphoma that is diagnosed in 18,000 Americans and has a worldwide incidence of ~120,000 cases per year. The clinical behavior of FLs is characterized by slow and relentless growth and inevitable relapse despite intensive chemotherapy.

FLs are considered indolent and slow growing tumors. This is in contradistinction to aggressive lymphomas, where cell cycle lesions/mutations are common and their pathogenic and therapeutic relevance is established (Pasqualucci et al., *Nature genetics* 43: 830-837 (2011), Morin et al., *Nature* 476: 298-303 (2011), Schmitz et al., *Nature* (2012), Monti et al., *Cancer Cell* 22:359-372 (2012), Lenz et al., *Proc Natl Acad Sci USA* 105:13520-13525 (2008), Jardin et al., *Blood* 116: 1092-1104 (2010)). Cell cycle lesions have only rarely been reported in FL and their role has remained unclear (Chim et al., *Human pathology* 38:1849-1857 (2007), Alhejaily et al. *Human pathology* 42:972-982 (2011), Pruneri et al., *International journal of cancer. Journal international du cancer* 112:71-77 (2004)).

FLs are genetically defined by the translocation t(14;18) that activates the anti-apoptotic BCL2 (B-cell lymphoma 2) protein. However, BCL2 activation is not sufficient for malignant growth (Staudt, *N Engl J Med* 356:741-742 (2007)), and therapies that target BCL2 have shown limited efficacy in the treatment of FL.

Effective treatments are needed for this fatal condition.

BRIEF SUMMARY OF THE DISCLOSURE

The inventors have surprisingly discovered that a significant proportion of FL cancers show dysregulation of the retinoblastoma (RB) cell cycle pathway. The result of this dysregulation is inactivation of the RB protein, and uncontrolled proliferative capacity in FL cells, which are already primed for cancer development by increased activity of the anti-apoptotic BCL2 protein.

The hallmark of FL is up-regulation of the BCL2 gene, typically by the translocation t(14;18). Thus, identification of the t(14;18) translocation indicates the presence of FL in a subject. Unfortunately, BCL2 inhibitors have not been demonstrated to be an effective treatment for FL. However, the inventors have now discovered that, in FL subsets characterized by BCL2 up-regulation and RB inactivation, combination therapy with BCL2 inhibitors and inhibitors of cyclin-dependent kinase (CDK) 4/6 is an effective treatment.

This disclosure therefore presents a novel diagnostic tool, and an effective combination therapy with BCL2 inhibitors and inhibitors of CDK4/6, for the treatment of FL associated with RB inactivation.

In one aspect, this disclosure provides methods to subtype or characterize FL in a FL patient, the methods including detection of a biomarker associated with inactivation of RB in a sample from the patient. The sample can be any biological sample, such as tumor tissue, blood, or whole cell lysate. Biomarkers associated with inactivation of RB include phosphorylated RB protein, a genetic alteration of the Rb locus, increased level or activity of cyclin-dependent kinase 4 (CDK4) or Cyclin D3, which may result from a genetic alteration of the CDK4 or Cyclin D3 locus, or a decreased level or activity of p16. Biomarkers associated with inactivation of RB can be detected using methodologies further described and illustrated herein.

If a biomarker associated with inactivated RB is detected in a FL patient, the patient can be assigned to a category of having RB-inactivated (RB-I) FL. If a biomarker associated with inactivated RB is not detected, or is not detected at threshold levels, the patient can be assigned to a category of having RB-not inactivated (RB-NI) FL. The present method can include an initial determination of FL in the patient, prior to determining if the patient has RB-I or RB-NI subtype FL.

This disclosure further provides a method of treating follicular lymphoma (FL) in a patient identified as having retinoblastoma (RB)-inactivated FL. The method includes administering a combination of a B-cell lymphoma-2 (BCL2) inhibitor and a cyclin-dependent kinase (CDK)4/6 inhibitor to the patient, in an amount effective to treat RB-inactivated FL in said patient.

The method of treatment can include an initial testing for the presence of a biomarker associated with inactivation of RB in a sample from the patient and subtyping said patient as having RB-inactivated FL if the biomarker is detected in the patient sample. If the patient is subtyped as having RB-inactivated FL, or assigned to a category of having RB-inactivated FL, an effective amount of a B-cell lymphoma-2 (BCL2) inhibitor and a cyclin-dependent kinase (CDK) inhibitor can then be administered to the patient. Combination treatment has been shown to be effective for the treatment of RB-inactivated FL, with low toxicity and enormous potential to improve and lengthen the lives of patients with this serious condition.

In one embodiment, the CDK inhibitor administered is an inhibitor of CDK4/6. Exemplary CDK inhibitors include, but are not limited to, PD-0332991, Flavopiridol, AT7519M, P276-00, SCH 727965, AG-024322, LEE011, LY2835219, P1446A-05, BAY 1000394, or SNS-032. Exemplary BCL2 inhibitors include, but are not limited to, ABT-737, Obatoclax mesylate, Navitoclax, or TW-37, as further described hereinbelow.

BRIEF DESCRIPTION OF THE FIG.S

The patent or application file contains at least one drawing executed in color. Copies of this patent or patent application publication with color drawing(s) will be provided by the Office upon request and payment of the necessary fee.

FIG. 1. Cell cycle control genes are targets of genetic lesions in a large number of FLs. a, Graphical representation of CYCLIND3 mutations in FL; b, Representative sequencing traces of homozygous (#107-2124) and heterozygous (#106-1301, #1125P) CYCLIND3 mutations in FL; c, Analysis of recurrent (>5%) and focal (<5 Mb) copy number changes in 64 FLs showing frequency peaks of deletions (blue) and amplifications (red) across the genome. d, Genome-wide analysis reveals a mutual exclusive relation between gains or losses affecting CDKN2A/B, RB, and CDK4 in FL.

Figure 2:
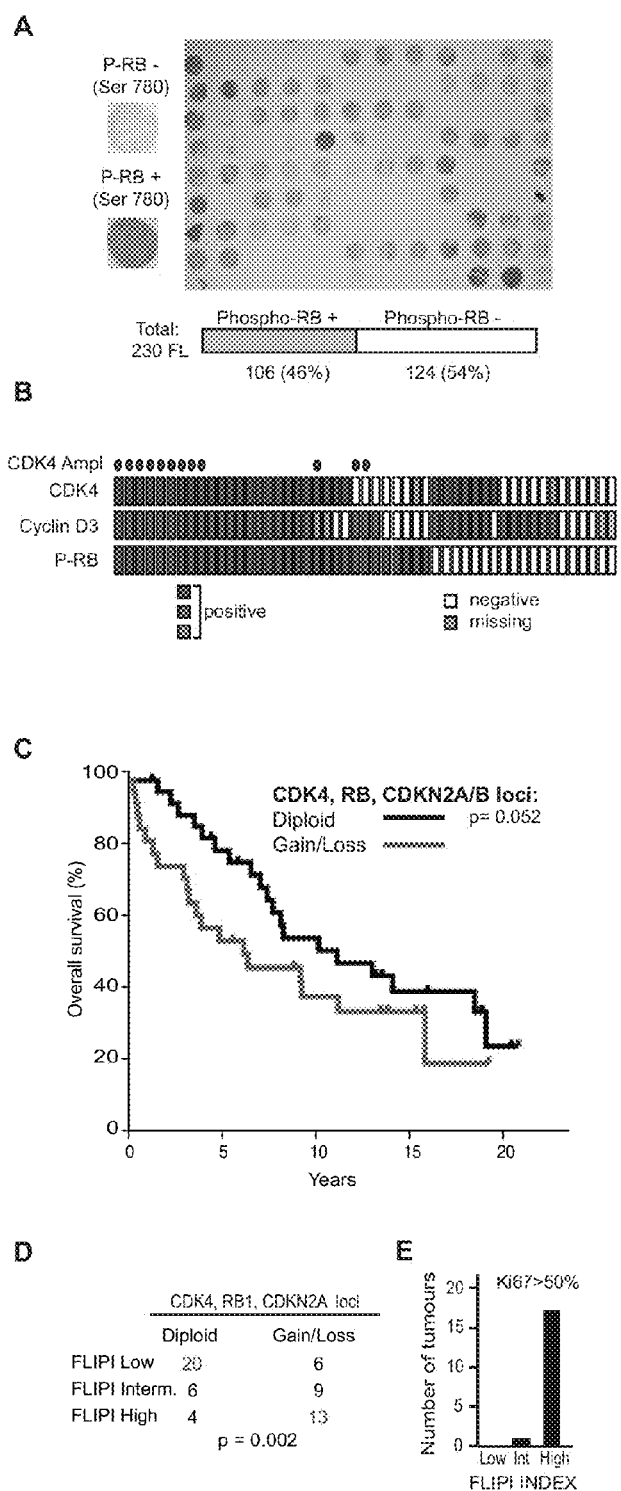

FIG. 2. Loss of cell cycle control identifies high-risk patients who do poorly with current therapy. a, Representative section of a tissue microarray (TMA) of 230 human FLs stained for phosphorylated RB (Ser 780) and graphic data summary; b, Summary of TMA data for samples with complete datasets; high levels of CYCLIN D3 and CDK4 account for most cases of phosphorylated RB; c, Survival analysis of 58 FL patients with (red) and without (black) copy number alterations affecting the CDKN2A/B, RB, or CDK4 loci; d,e, Association of copy number alterations affecting the CDKN2A/B, RB, or CDK4 loci with FLIPI index (d), and with high Ki67 index defined as >50% Ki67 positivity of tumor (e).

Figure 3:
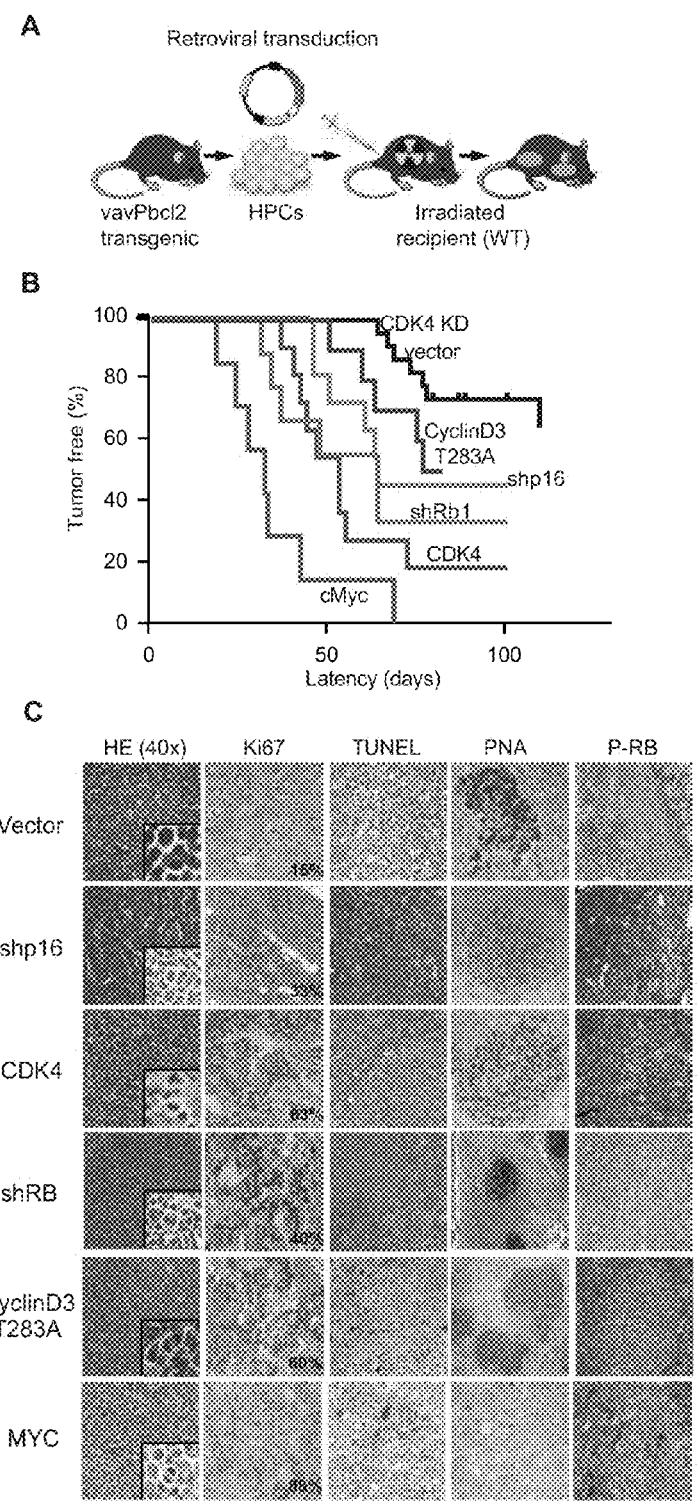

FIG. 3. Cell cycle activation cooperates with Bcl2 in FL development in vivo. a, Diagram of the adoptive transfer model of FL; b, Kaplan-Meier analysis showing time to tumor development after transplantation of vavP-Bcl2 transgenic HPC transduced with vector (black), or CDK4 (blue), kinase dead CDK4 (CDK4-KD, grey), c-MYC (red), CYCLIN D3 T283A (purple) and shRNAs against p16 (green) and RB (pink). c, Immunohistochemical analysis of murine lymphomas harboring the indicated genetic changes and high resolution inset.

Figure 4:
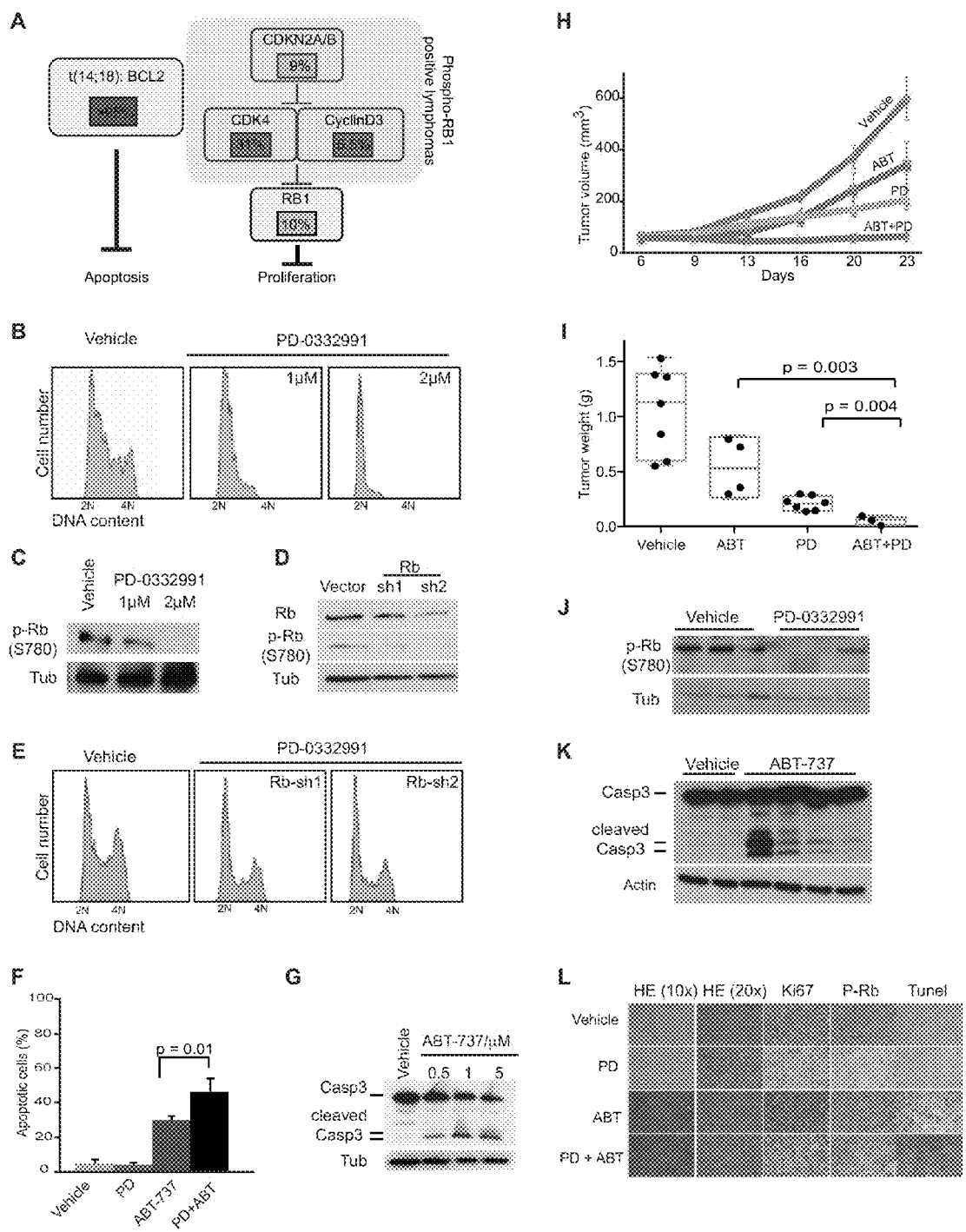

FIG. 4. Dual CDK4 and BCL2 blockade is effective against FL. a, Summary of genetic data indicating the t(14;18) causing elevated BCL2 and genomic lesions activating the cell cycle as oncogenic drivers in a sizeable fraction of FLs; b, Cell cycle profile of DoHH2 cells following 24 h treatment with PD-0332991 or vehicle (DMSO); c, Immunoblot for RB phosphorylation (Ser 780) in DoHH2 cells treated as indicated; d, Immunoblot for indicated proteins on lysates from DoHH2 cells expressing RB shRNAs sh2); e, Cell cycle profile of DoHH2 cells expressing the RB shRNA and treated with PD-0332991 (1 µM) or vehicle (DMSO); f, DoHH2 and Su-DHL-6 cell apoptosis following in vitro treatment with, PD-0332991 (1 µM), ABT-737 (1 µM), both drugs, or DMSO (*=pvalue<0.01) g, Immunoblot on DoHH2 cells treated with ABT-737 and probed for total and cleaved caspase-3 (casp3); h, Tumor volume curve for xenografted DoHH2 tumors treated with the indicated drugs for 14 days; i, Weight of residual tumor tissue harvested at the end of the treatment course (ABT=ABT-737; PD=PD-0332991); j, k, Immunoblot on lysates of tumors treated in vivo with PD-0332991 or ABT-737 probed for RB phosphorylation (Ser780) (j) or cleaved caspase-3 (k); l, Immunohistochemical analysis of DoHH2 tumors harvested at the end of the treatment interval.

Figure 5:
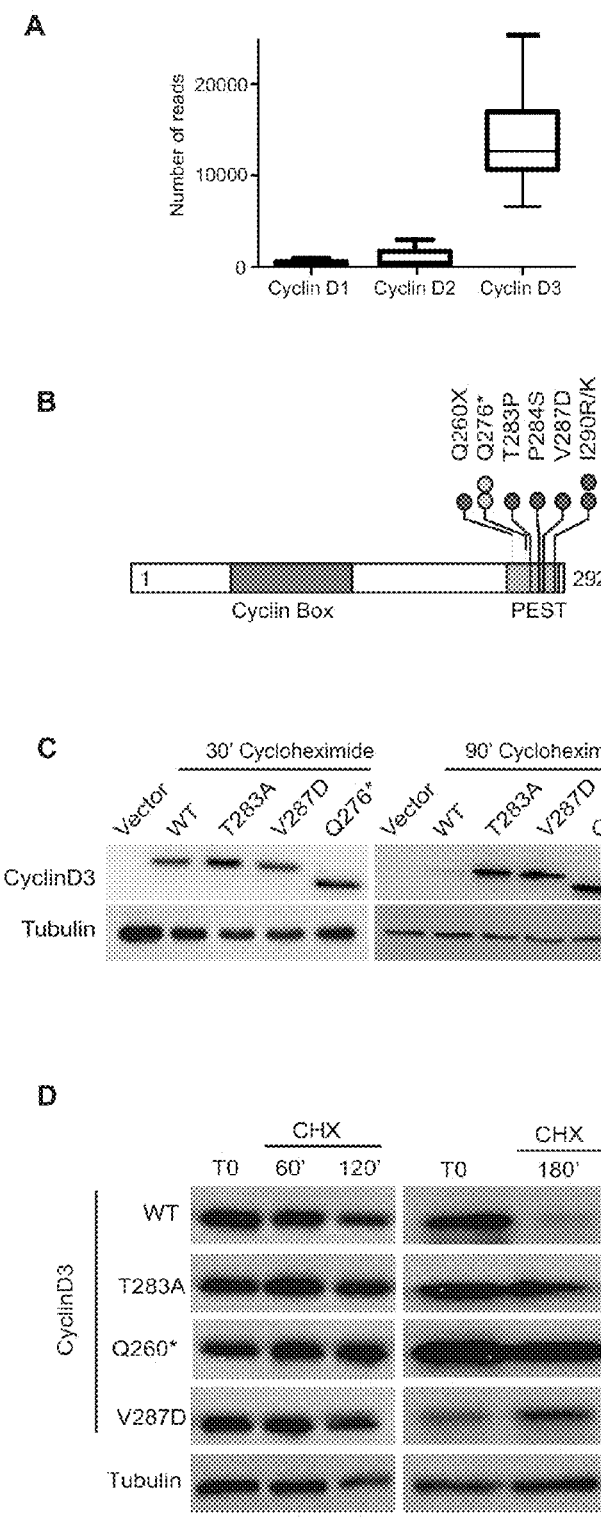

FIG. 5. CCND3 mutations. a, RNA expression levels of CCND1, CCND2, CCND3 in FL samples; b, Graphical representation of CCND3 mutations reported in aggressive lymphomas; c, d, Immunoblot on lysates of 293T (c) or FL5-12 pre-B-cells (d) expressing the indicated wild type or mutant forms of CYCLIN D3 and either untreated or treated with for the indicated times with cycloheximide.

Figure 6:
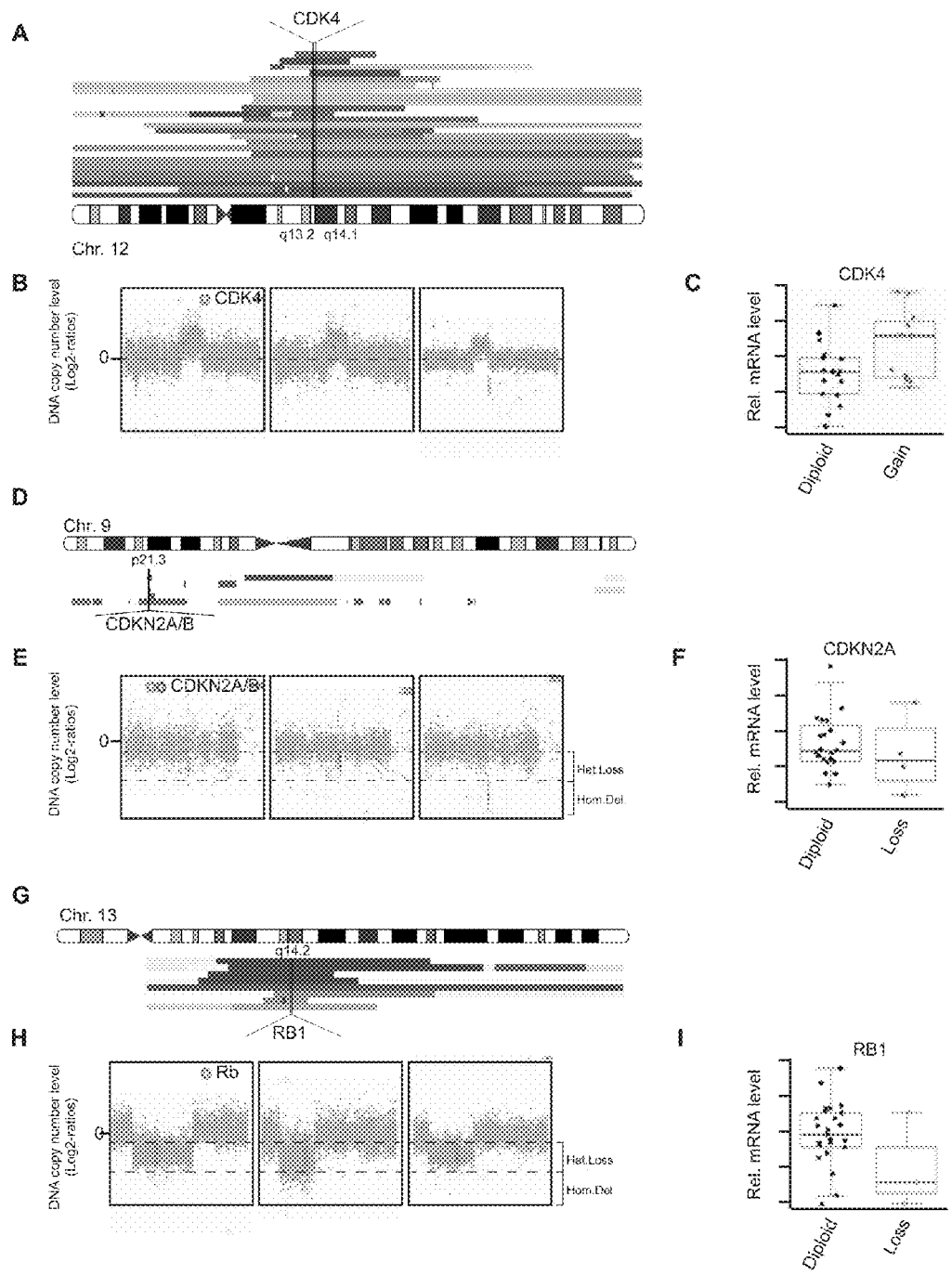

FIG. 6. Chromosomal aberrations affect cell cycle loci in FL. a, Summary graph of all FL samples showing chromosomal gains affecting CDK4; b, Representative examples indicating patterns of gains in individual cases; c, qRT-PCR comparing CDK4 mRNA levels in diploid cases versus FLs harboring gains; d, Summary of FL samples with chromosomal losses affecting CDKN2a/b, a threshold indicates rare homozygous losses (see method for definition); e, Representative examples; f, qRT-PCR for CDKN2a/b; g, Summary of losses affecting RB; h, Representative examples; i, qRT-PCR for RB mRNA levels.

Figure 7:
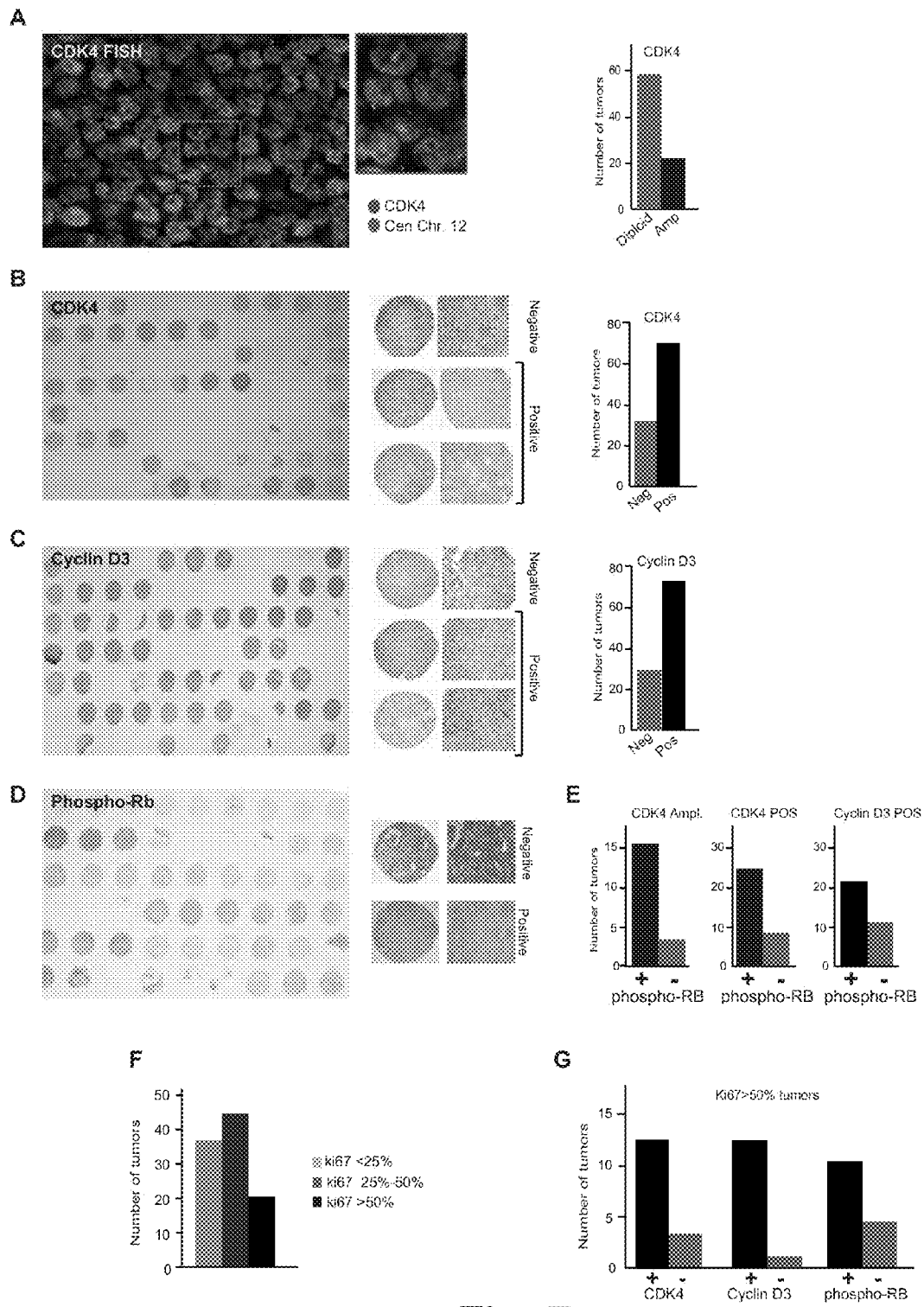

FIG. 7. Tissue micro-array studies on a second cohort of FL samples. a, Representative section of a tissue microarray (TMA) of 105 human FLs hybridized with CDK4 BAC clone (red) and chromosome 12 centromeric (green) and graphic data summary; b-c, Representative section of a tissue microarray (TMA) of 105 human FLs stained for CDK4 (b) and Cyclin D3 (c) and graphic data summary. d, Representative section of a tissue microarray (TMA) of 105 human FLs stained for phosphor-Rb. e, Association of CDK4 FISH data and protein levels for CDK4, CYCLIN D3, and phosphorylated RB; f, Summary of Ki67 stain on FL TMAs; g, Fraction of proliferative tumors (Ki67>50%) that expressing high or low levels of CDK4, CYCLIN D3, and phosphorylated RB.

Figure 8:
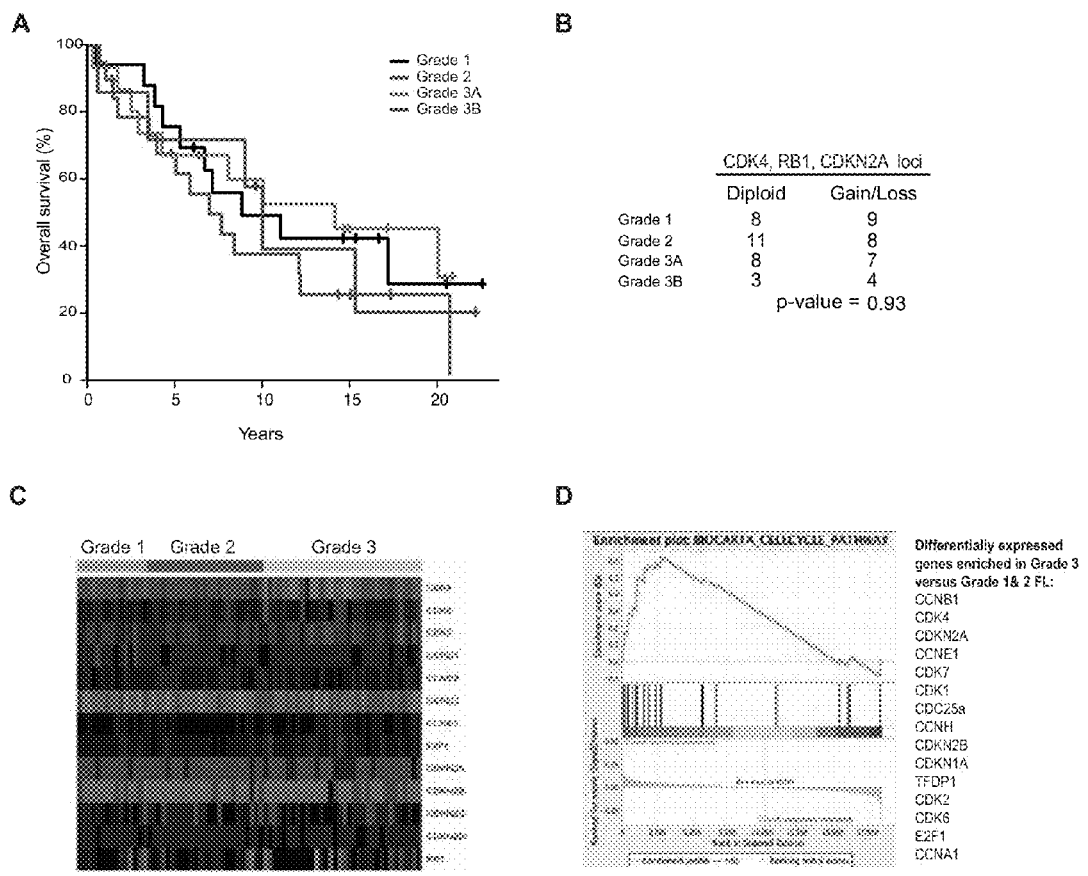

FIG. 8. Tumor grade does not predict outcome and is not associated with cell cycle lesions. a, Survival analysis of 58 FL patients stratified by Grade 1 (black), Grade 2 (red), Grade 3A (green) and Grade 3B (blue); b, Lesions affecting CDK4, RB, CDKN2a/b occur across all FL grades; c, Heat map generated from gene expression profiles (GEP) on FLs grouped by grade and indicating expression patterns of cell cycle genes; d, Gene set enrichment analysis (GSEA) identifies a proliferation signature in high grade FL that are composed of proliferating centroblasts.

Figure 9:
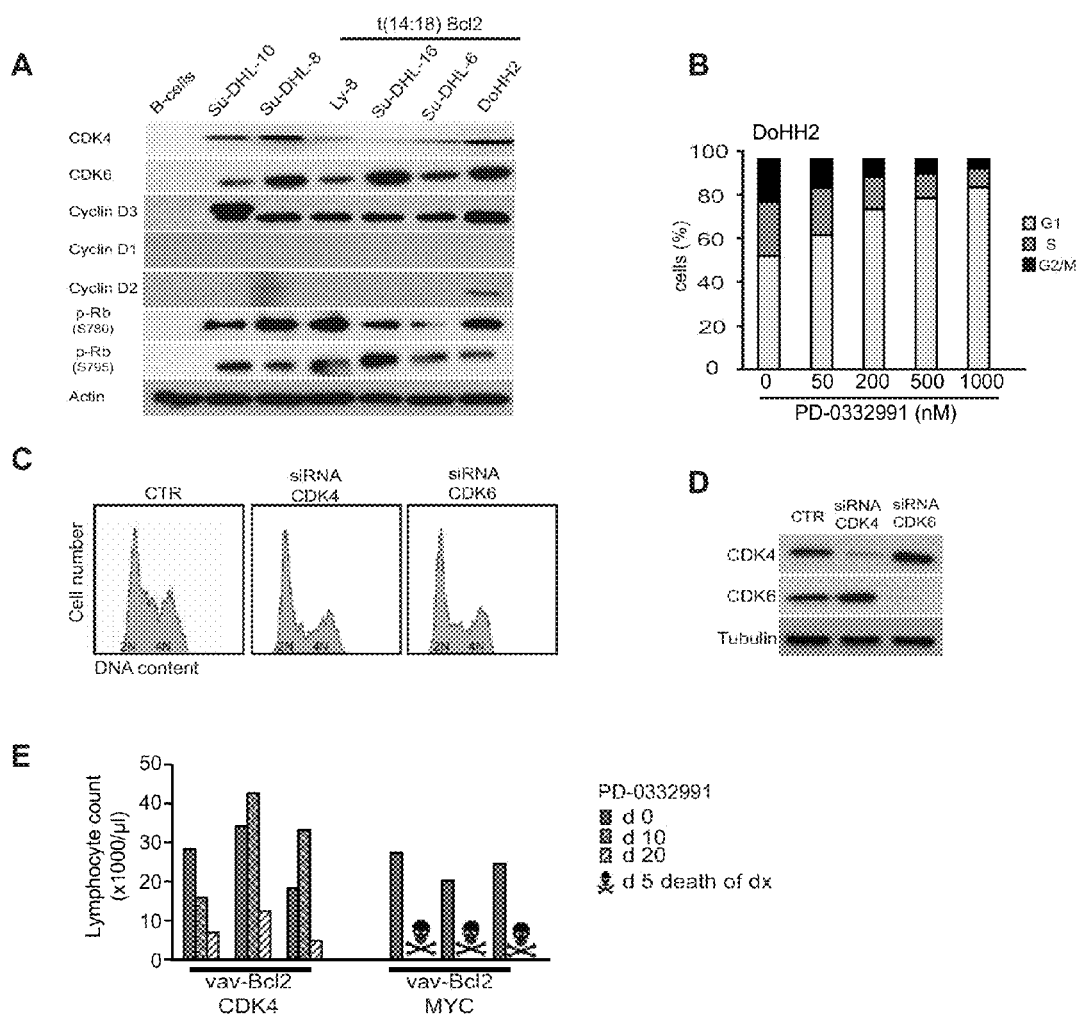

FIG. 9. CDK4 inhibitor treatment of human lymphoma cells. a, Immunoblot on a panel of human lymphoma lines probed as indicated; b, Cell cycle profile of FL-transformed DoHH2 cell line treated with increasing PD-0332991 doses for 24 h; c, Cell cycle profile of DoHH2 cell line transduced with siRNAs against CDK4 or CDK6; d, Immunoblot for CDK4 and CDK6 (Ser 780) in DoHH2 cells transduced with siRNAs against CDK4 or CDK6; e, Lymphocyte counts in vav-Bcl2/CDK4 and vav-Bcl2/Myc tumor bearing animals treated with PD-0332991; note all animals harboring vav-Bcl2/Myc lymphomas succumbed to disease within the first 10 days.

Figure 10:
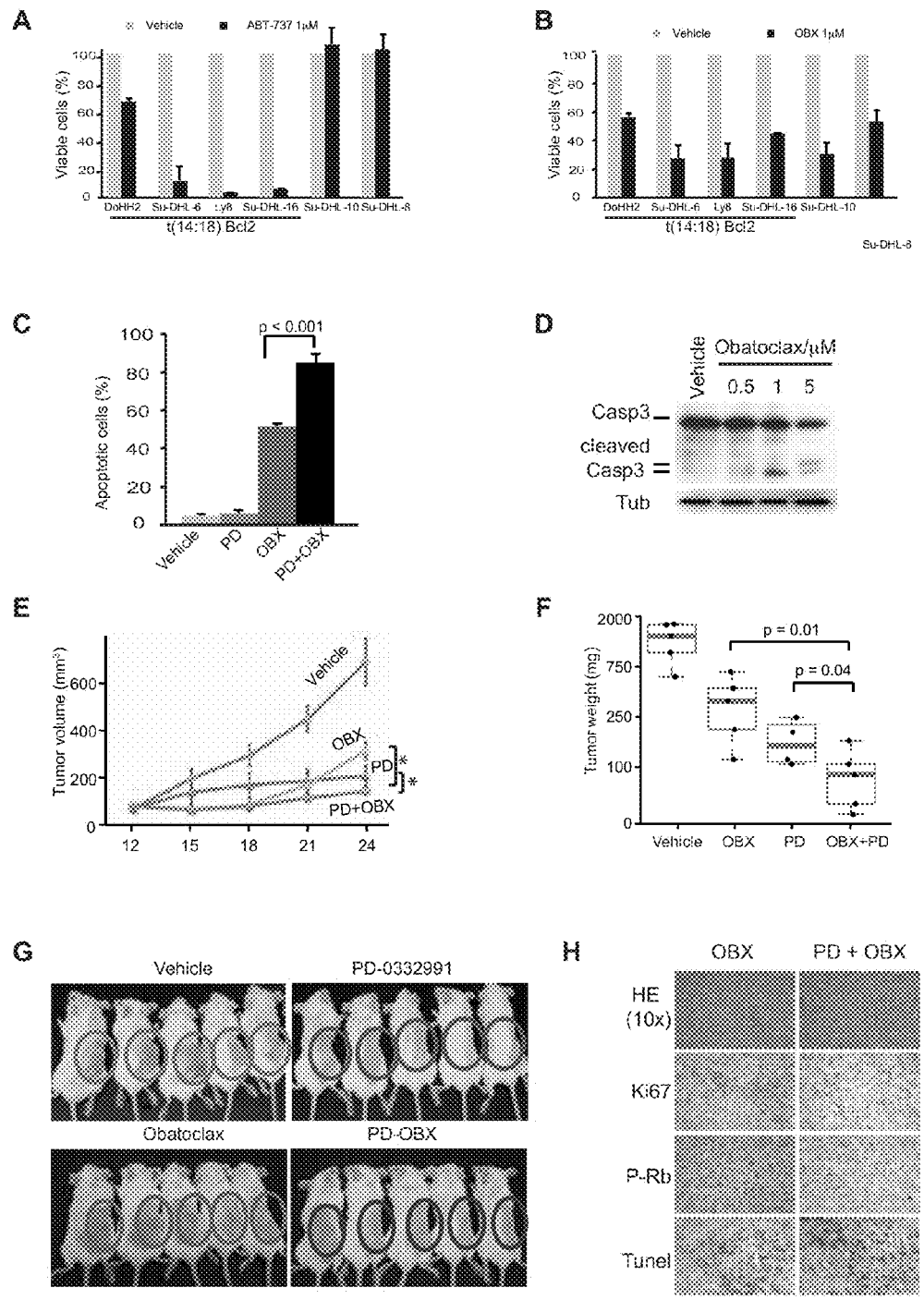

FIG. 10. BCL2 inhibitor treatment of lymphoma cells. a, b, Viability in a panel of human lymphoma lines after 24 of treatment with ABT-737 or Obatoclax (OBX); cell lines harboring the translocation t(14;18) are indicated; c, DoHH2 cell apoptosis following in vitro treatment with PD-0332991 (1 µM), OBX (1 µM), both drugs, or DMSO; d, Immunoblot on DoHH2 cells treated with OBX and probed for total and cleaved caspase-3 (Casp3); e, DoHH2 tumor volume after 2 week treatment with indicated drugs; f, Weight of residual tumor after treatment; g, Photograph of cohorts of animals bearing xenografted DoHH2 tumors following treatment with the indicated drugs; h, Immunohistochemical stains for the indicated markers on xenografted DoHH2 tumors after treatment.

Figure 11:
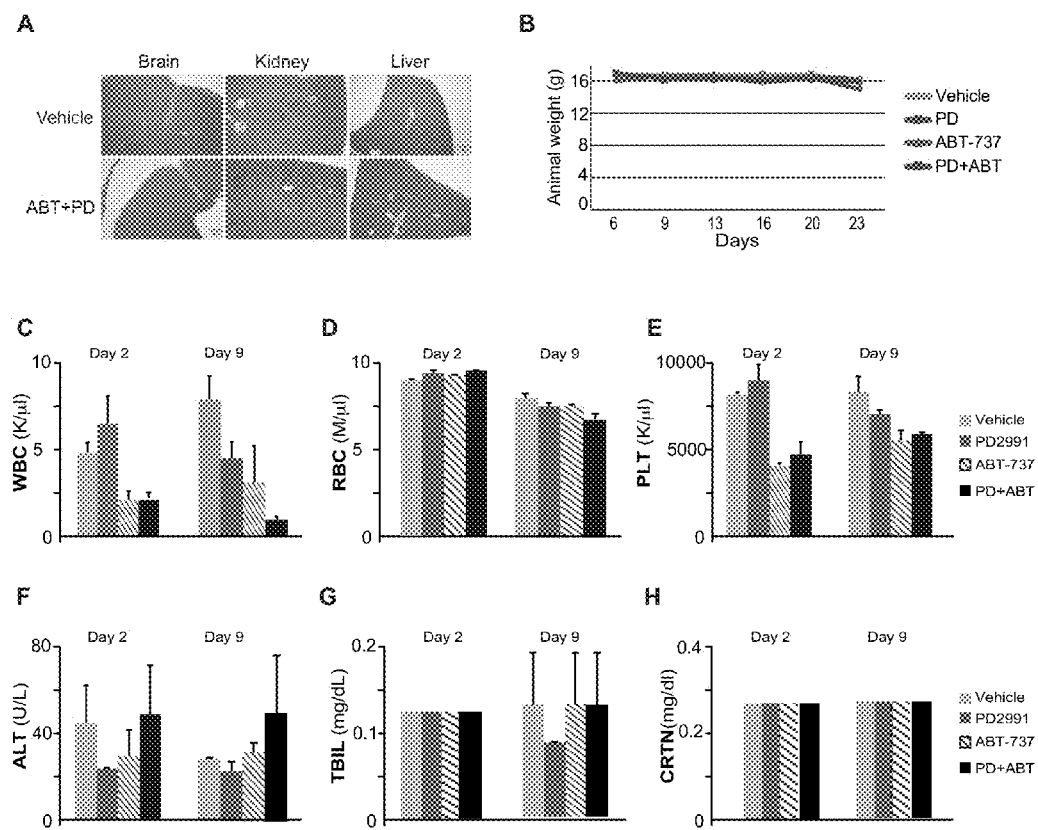

FIG. 11. Toxicity analysis of dual CDK4 and Bcl2 inhibitor treatment. a, Representative microscopic histology of brain, kidney, and liver following PD-0332991/ABT-737 (PD+ABT) or vehicle; b, Animal weights across the treatment interval; c-h, White blood cell (WBC), red blood cell (RBC) and platelet (PTL) counts, Alanine Aminotransferase (ALT), Total bilirubin (TBIL) and Creatinine (CRTN) levels in mice treated with PD-0332991, ABT-737, both drugs or vehicle and collected 2 or 9 days after the last treatment.

DETAILED DESCRIPTION OF THE DISCLOSURE

The inventors have surprisingly discovered that retinoblastoma (RB)-controlled cellular proliferation is dysregulated in a subset of FL. In particular, FL with inactivated RB shows increased malignancy and is associated with greater risk of progression to metastasis and mortality. This identification of a role of RB, as well as the cyclin/CDK kinase pathway involved in cellular proliferation, is unexpected in light of the characterization of FL as a slow-growing cancer that does not behave as a typical cell-cycle dysregulated cancer. The identification of dysregulation of the RB pathway in a subpopulation of FL cancers opens the door to new methods of distinguishing FL types, new ways of determining FL relative risks, and new forms of FL treatments.

The finding of cell cycle lesions in this type of FL is surprising because FLs are considered indolent and slow growing tumors. In contrast to FL, cell cycle lesions/mutations are common in aggressive cancers, in which the pathogenic and therapeutic relevance of cell cycle mutations is well established. Most FLs carry the translocation t(14;18) that increases BCL2 expression and blocks programmed cell death. However, the inventors now report additional mechanisms that promote malignant growth in this subset of FL; these include CCND3 (Cyclin D3) PEST domain mutations that increase protein stability, (6%), loss of CDKN2a/b (9%), and/or activating/gain of function CDK4 mutations (31%). CyclinD3 binds CDK4, and the resulting CyclinD3/CDK4 complex phosphorylates and inactivates RB. Thus, mutations that increase the presence or activity of CyclinD3/CDK4 lead to RB inactivation.

Follicular lymphoma (FL) is a lymphoma of follicle center B cells. FLs are genetically defined by the translocation t(14;18), which activates the anti-apoptotic BCL2 (B-cell lymphoma 2) protein. The bcl-2 gene is normally found on chromosome 18, and the translocation moves the gene near to the site of the immunoglobulin heavy chain enhancer element on chromosome 14. This dysregulation increases the activation/expression of BCL2, thus suppressing apoptosis. Apoptosis is programmed cell death. Cells can initiate apoptosis in response to toxic insult, DNA damage/genetic alterations, or other signals that the cell is not functioning properly. Loss of anti-apoptotic BCL2 reduces cell sensitivity to apoptotic signals, and increases the risk of neoplastic development with the accumulation of additional genetic lesions. Although characterized by BCL2 activation, FL does not respond well to treatment with BCL2 inhibitors.

The growth cycle of eukaryotic cells is regulated by cyclin-dependent kinases ("CDKs") and cyclins, which assist in the progression of the growth cycle phase. The cell cycle is further regulated by the RB protein. In normal cells, RB is expressed throughout the cell cycle but exists in multiple phosphorylated forms that are specific for certain phases of the cycle. The more highly hyperphosphorylated forms are found during the S and G2/M active growth phases of the cell cycle, whereas the hypophosphorylated forms are the primary species seen in G1 and in the growth arrested state. Accordingly, hypophosphorylated RB is associated with growth-suppressive activity, since this form is prevalent in G1 and growth arrested cells.

When it is time for a cell to enter S phase, CDK-cyclin complexes phosphorylate RB, inhibiting its activity and allowing the cell to enter a proliferative phase. The initial RB phosphorylation is performed by a complex including Cyclin D, CDK4, and CDK6. Cyclin D3 binds to and activates CDK4, leading to phosphorylation of RB by CDK4. This is followed by additional phosphorylation by Cyclin E/CDK2. RB remains phosphorylated throughout S, G2 and M phases, and is dephosphorylated in G1/G0 phases, allowing cell cycle arrest. Thus, RB is an important checkpoint for cell cycle growth, and inactivation of RB, through mutation in the gene, phosphorylation, or by other means, can lead to malignant growth.

The inventors have unexpectedly discovered that 46% of FLs carry one or more genomic lesions affecting cell cycle control loci (e.g., p16, RB, CDK4, Cyclin D3/CCND3). These FLs are marked by elevated RB phosphorylation, indicating functional inactivation of this tumor suppressor, or else are marked by RB mutation or deletion, indicating inactivation by genetic alterations. Cell cycle lesions were strongly associated with elevated risk by FLIPI, an established prognostic index that largely reflects extent of the disease. Accordingly, patients whose FLs harbor cell cycle lesions fare poorly with current therapy and they are considered high-risk. Hence, loss of proliferation controls drives disease progression and increased clinical risk in a sizeable number of FL patients.

The present disclosure identifies a subset of follicular lymphoma (FL) characterized by dysregulation of the cyclin/CDK/RB proliferative pathway. Combined with mutations that activate the anti-apoptotic BCL2 gene, this type of FL is associated with increased malignancy and mortality, relative to FL which is not associated with cell cycle dysregulation. Accordingly, this disclosure presents novel methods to subtype FL and stratify patient risk. This disclosure further presents novel therapies that show increased efficacy in the treatment of FL characterized by activation of this proliferative pathway.

In one aspect, this disclosure provides methods of categorizing or "subtyping" FL according to the presence or absence of a biomarker associated with RB inactivation. Following testing for the presence of a biomarker associated with RB inactivation in a patient sample, the patient can then be assigned to a subtype of RB-inactivated FL (referred to herein as "RB-I FL") or to a subtype of RB-not inactivated FL (referred to herein as "RB-NI FL").

The term "subtype" as used herein in connection with FL refers to a biologically, genetically, and clinically distinct type of follicular lymphoma (FL) characterized by RB inactivation and loss of cell cycle control. Biologically, this type of FL is distinct in that it shows a loss of cell cycle regulation and inactivation of RB not present in all FL cancers. Genetically, this type of FL is distinct in that it is characterized by genetic alterations in cell cycle regulatory proteins, and is associated with increases at the genetic level in cell cycle tumor activating proteins, and with decreases at the genetic level in tumor suppressor proteins. Clinically, this type of FL is also distinct, because patients with FL showing RB inactivation have a worse prognosis and shorter survival index than patients with FL in which RB is not inactivated, and because this type of FL responds well to therapeutic interventions targeting both BCL2 and the CDK pathway.

As used herein, the terms "subject" and "patient" are used interchangeably and refer to an animal, including mammals such as non-primates (e.g., cows, pigs, horses, cats, dogs, rats etc.) and primates (e.g., monkey and human).

To detect a biomarker associated with RB inactivation, a sample is obtained from a FL patient. The term "sample" refers to a biological sample obtained from a FL patient, including any sample containing FL cells, such as, e.g., an FL tissue sample, blood, cerebro-spinal fluid (CSF), among others. Methods of obtaining a FL tissue sample are well known in the art and include obtaining samples from surgically excised tissue. Tissue samples and cellular samples can also be obtained without the need for invasive surgery, for example by puncturing the chest wall, abdominal wall, lymph node, breast, thyroid or other sites with a fine needle and withdrawing cellular material (fine needle aspiration biopsy). In certain embodiments, samples taken from a patient can be treated or processed to obtain processed samples such as supernatant, whole cell lysate, or fractions or extract from cells obtained directly from the patient. In other embodiments, samples taken from a patient can also be used with no further treatment or processing.

As used herein, a "biomarker" is any biological indicator. A "biomarker associated with inactivation of RB" is a biomarker that identifies an alteration in the cell cycle pathway that is indicative of or results in RB inactivation. In one embodiment, a biomarker associated with RB inactivation is the phosphorylation state of RB protein (or, in other words, phosphorylated RB protein, including hyperphosphorylated RB protein). In another embodiment, a biomarker associated with RB inactivation is a protein that causes inactivation of RB, such as CDK4 or Cyclin D3; the presence or an increased presence and/or activity of such protein would result in RB inactivation. In yet another embodiment, a biomarker associated with RB inactivation is a protein whose absence or decreased presence and/or activity activates RB, such as an RB dephosphorylase or a cyclin-dependent kinase (CDK) inhibitor (such as p16).

Detection of a biomarker in a patient sample can be compared to a control representing the level of background or the level of the biomarker in a sample from a healthy individual without cancer. The control can also be a sample of non-diseased tissue from the patient being tested. The differences between the level or activity of a biomarker relative to a control should be at least 15%, or at least 20%, or at least 25%, 30%, or 40% or more, to be significant and permit a determination and conclusion of RB inactivation.

In one embodiment, RB inactivation is determined by detecting the presence of phosphorylated RB protein in a sample.

Human RB protein is inactivated by phosphorylation at residues Ser780, Ser795 and Ser807/811; accordingly, detection of phosphorylation at one or more of these residues indicates inactivation of RB.

A variety of methods are known and suitable for detecting the phosphorylation status of RB protein. Phosphorylation of RB may be detected using an antibody recognizing phosphorylated RB (a "phospho-RB" antibody), in particular an antibody specific for phospho-RB-Ser780 or phospho-RB-Ser795 (that is, an antibody that recognizes RB phosphorylated on Serine 780 or Serine 795 of the RB amino acid sequence), as well as phospho-RB-Ser608, phospho-RB-Ser612, phospho-RB-Ser807, or phospho-RB-Ser811. Such antibodies are commercially available, for example, from Cell Signaling Technology, Inc. Other molecules that recognize phosphorylated RB may also be used, where appropriate.

Phospho-RB antibodies can be used in numerous assays known in the art to identify the presence or level of proteins, for example, Western Blot (Burnette W N, *Analytical Biochemistry* 112:195-203 (1981)), ELISA (Engvall E, Perlman P. Immunochemistry 8:871-4 (1971)), immunohistochemistry, and microarrays.

For Western blot, immunoblots can be performed using whole cell lysates or tissue samples as described, for example, in Steidl et al., *Nature* 471:377-381 (2011). For example, the protein/sample can be resolved on an SDS-PAGE gel and transferred to a nitrocellulose membrane. Antibodies against Rb, Phospho-Rb, Phospho-Rb S780, Phospho-Rb S795, CDK4, CyclinD3, and other proteins of interest, can be applied to the membrane, allowed to hybridize, washed, and tested for hybridization relative to hybridization of a control binding antibody. Detection of hybridized antibody to the biomarker, or detection of an increased amount of hybridization signal relative to the control indicates that the biomarker is detected, or is detected in increased amounts in the patient sample.

Enzyme-linked immunosorbent assays (ELISA) can also be used. In one example, a sample from the patient, such as blood, tissue, or whole cell lysate, is prepared in binding buffer, and used for coating ELISA plate wells. An antibody or other molecule recognizing the protein is then added to the plate wells and allowed to bind to the wells, and detection of the antibody in the wells indicates the presence, or the increased presence relative to a control amount, of the protein of interest. This assay can also be utilized in reverse, with the antibody used to coat the ELISA plate wells, and the patient sample added to the wells and allowed to bind to the antibody, followed by detection.

For immunohistochemistry, samples can be embedded in appropriate material, stained to identify the biomarker, sectioned, and examined microscopically. For example, tissue sections can be stained with primary antibodies to the biomarker (for example, phospho-RB antibodies), where the primary antibodies are optionally conjugated to a label such as horseradish peroxidase or other label. The sample is then stained with a secondary reagent that recognizes the primary antibody or primary antibody conjugate, and can be additionally stained with reagents such as hematoxylin and eosin (H&E) stain to identify other cellular components. A control representing a sample of non-cancerous tissue, either from the same patient or from a healthy donor, can be used to compare the presence or absence, or the level of presence as appropriate, of the biomarker.

Tissue microarrays also allow detection of biomarkers. Tissue microarrays can be constructed as described in Schatz et al., *J Exp Med* 208:1799-1807 (2011). Tissue microarray slides can be prepared as for immunohistochemistry, with sections applied to slides and allowed to adhere. Slides can be incubated with antibodies to the biomarker and incubated to allow hybridization. After incubation, the slides can be washed, counterstained, then scanned, and the scanned image can then analyzed by standard scanning software. Signals from the patient sample and control sample slides can be compared and the ratio of control sample to patient sample can be calculated to determine the presence of the biomarker in the patient sample.

Immunohistochemistry and tissue microarrays can further be performed on a patient sample in combination with Ki-67 staining. Ki-67 is a nuclear non-histone protein that is present at low levels in quiescent cells but is increased in proliferating cells, especially in the G2, M, and latter half of the S phase. Thus, Ki-67 reactivity, defined as percent tumor cells staining positive as measured by immunohistochemical (IHC) staining, is a specific nuclear marker for cell proliferation.

In another embodiment, the biomarker being detected is a genetic abnormality indicative of or resulting in RB inactivation.

RB can be inactivated by a mutation in the Rb genetic locus that downregulates the presence or activity of RB protein. For example, Rb mutations can cause reduced or no expression of protein, or can cause an increase in degradation or decrease in translation of the Rb mRNA. Rb mutations can also cause expression of non-functional RB protein.

The terms "mutation" and "lesion" are used interchangeably herein to refer to DNA alterations including deletions (removal of one or more nucleotides, including removal of large portions of nucleic acid resulting in, e.g., copy number loss), insertions (addition of one or more nucleotides, including addition of large portions of nucleic acid result in, e.g., copy number gain), translocations (chromosome abnormalities caused by rearrangement of parts between nonhomologous chromosomes), missense mutations (one or more nucleic acid base changes or substitutions in a genetic locus, resulting in a codon that causes insertion of a different amino acid into the growing polypeptide chain leading to an altered protein), or nonsense mutations (one or more nucleic acid base changes or substitutions in a genetic locus, resulting in a stop codon that prematurely truncates the polypeptide chain and produces a shortened protein fragment).

RB inactivation as a result of genetic lesion can be determined by karyotyping FL cells from the patient sample to identify large chromosomal aberrations such as translocations or deletion of chromosomal segments. Karyotype analysis involves examining the structure of metaphase chromosomes, stained with Giemsa or other stain, to identify characteristic banding patterns in the chromosomes. Karyotyping identifies structural abnormalities with any of the individual chromosomes by detecting alterations in these characteristic banding patterns.

DNA sequencing and PCR amplification of genetic regions of interest is used to detect small genetic changes in the Rb locus. Primers directed to the region or regions of interest can be designed according to the methods described in Steve Rozen and Helen J. Skaletsky, in: Krawetz S, Misener S (eds) *Bioinformatics Methods and Protocols: Methods in Molecular Biology*, Humana Press, Totowa, N.J., pp 365-386 (2000). M13 tails can be added to facilitate Sanger sequencing. PCR reactions can be performed by standard methods according to the calculated annealing temperatures, purified, and sequenced. Sequence reactions can be run on a sequencing apparatus and the sequence can be determined by standard software analysis. Sequences can be assembled against the reference sequences for each gene, and assemblies passed on to analysis software such as Polyphred 6.02b and/or Polyscan 3.0 to generate a list of putative mutations. The putative mutation calls can be normalized to '+' genomic coordinates and annotated. Putative mutations can be confirmed by a second PCR and sequencing reaction, in parallel with amplification and sequencing of matched normal tissue DNA controls.

Copy number analysis allows for the identification of increased or decreased copies of a gene of interest. A standard algorithm can be used to initially identify segmental gains and losses along the chromosomes. To estimate the frequency of copy number changes for a specific gene, log 2 ratio signals from the algorithm output can be converted into discrete copy number calls (loss=−1, diploid=0, gain=1) defining the status of the gene in each sample. Gains and losses can be determined using a sample-specific threshold based on, for example, 2.22 median absolute deviations (approximately corresponding to 1.5 standard deviations) from the residual between probe-level data and means of segments having uniform DNA copy number level. Putative homozygous deletions can be defined for probe level below −2*Ts.

RB inactivation by mutation or deletion of the Rb gene can also be determined by detecting the presence or absence of functional RB mRNA or protein. The presence or amount of mRNA in the cells of the tissue sample can be assessed by methods known in the art, for example, by reverse transcribing the mRNA present in the cells to obtain cDNA which includes RB cDNA, i.e., cDNA hybridizable to RB mRNA. The presence of RB cDNA is indicative of the presence of RB mRNA in the cells from the tissue sample. The presence of RB cDNA can be determined, for example, by polymerase chain reaction (PCR). The level of RB cDNA can be assessed by quantitative PCR methods, as disclosed, for example, in Alard et al., Biotechniques, 15:730 (1993). "Quantitative PCR" refers to methods which are able to quantitate the amount of cDNA derived from reverse transcription of mRNA in cells from a tissue sample.

Genetic alterations of the Rb locus can also be determined using fluorescence in situ hybridization (FISH). FISH can be performed using BAC clones spanning the locus of interest. The BACs can be labeled by nick translation and hybridized with a control chromosome centromeric repeat as a reference. Tissue microarray slides can be hybridized, for example, by de-waxing the slides, microwaving in sodium citrate buffer, and treating with pepsin-HCl. Slides with probe mix can be co-denatured at 80° C. for 8 minutes, then incubated for 2-3 days at 37° C. After coverslip removal, the slides can be washed using standard non-formamide stringency washes, stained with DAPI, then mounted in antifade solution. The slides can be scanned and the scanned image can then analyzed by standard scanning software. Signals from the probe and reference signals can be counted for each image and the ratio of reference to locus-of-interest can be calculated to determine genetic alterations in the locus of interest.

In other embodiments, the method involves detection of a biomarker in the RB pathway upstream of RB, for example, RB inhibitors such as CDK4, CDK 6, or Cyclin D3, or the CDK inhibitor p16. CDK4 and CDK6 phosphorylate RB, thus inhibiting RB. Cyclin D3 activates CDK4 to phosphorylate RB. p16 inhibits CDK4, thus hampering RB inactivation. Accordingly, increased levels or activities of CDK4, CDK6, or Cyclin D3, and decreased levels or activities of p16, are exemplary biomarkers associated with RB inactivation.

Increased levels and/or activities of CDK4, CDK6, or Cyclin D3, or decreased levels or activities of p16, can result from genetic alterations, such as genomic copy number gain, gene a translocation, or a mutation that increases the protein half life or decreases protein or mRNA degradation. Thus, detection of these biomarkers can be achieved by detecting the levels and/or activities of the proteins molecules, or alternatively, by detecting the alterations in the respective genes. The general methodologies described above in relation to analyzing the RB protein, mRNA and genomic DNA, as well as the methodologies illustrated in the examples herein below, are applicable to assessing these other biomarkers.

By analyzing a patient sample as described hereinabove, the RB activation state of the patient's lymphoma cells can be determined. The patient can then be assigned to a subtype designated as having RB-inactivated FL ("RB-I FL"), or as having RB-not inactivated FL ("RB-NI FL").

Identification and classification of RB activation state can be used to predict risk outcomes. In particular, detection of RB-I FL indicates increased risk of progression to more advanced stages of FL, decreased response of the patient's FL to current therapeutic treatments, and decreased survival time in a patient.

In addition, this disclosure provides a method for monitoring the progression of FL in a patient. Basically, by periodic monitoring of one or more biomarkers associated with RB inactivation in a patient assigned to a RB-NI FL subtype, progression of the FL to a more malignant form can be identified by detecting RB inactivation in FL cells of the patient. If RB inactivation is detected in the patient FL cells, the outcome and prognosis worsens for that patient relative to before RB inactivation is detected. However, detection of RB inactivation opens up avenues for treatment, as discussed below, that are uniquely beneficial for this population of RB-I FL patients. Thus, monitoring for RB inactivation is an aspect of the disclosure that provides immediate diagnosis and altered therapeutic options in a FL patient, potentially before the patient presents with more severe clinical symptoms.

In a further aspect, this disclosure provides a novel combination therapy tailored to high-risk FLs associated with cell cycle lesions.

In connection with the discovery of a cell cycle dysregulation aspect of RB-I FL cancers, inhibitors of RB-inactivating proteins are shown herein to be particularly effective, in combination with BCL2 inhibitors, to treat RB-I FL. The inventors have found that combined treatment with CDK4/6 inhibitors and BCL2 blocking drugs produces powerful therapeutic effects against FL and is well-tolerated in vivo. BCL2 inhibitors have shown good activity against BCL2 expressing lymphoma cells in vitro, but their in vivo and clinical activity has been modest (Wilson et al., *Lancet Oncol* 11:1149-1159 (2010)). CDK4/6 inhibition can restore RB function in tumors harboring upstream cell cycle activating lesions. This study indicates that RB activation provides a readily detected marker that can pinpoint high-risk FL patients who stand to benefit from this combination CDK4/6 and BCL2 therapy.

Accordingly, this disclosure provides combination therapies and compositions for the treatment of RB-inactivated FL that include treatment with an inhibitor of one or more RB-inactivating proteins in combination with treatment with a BCL2 inhibitor. In one embodiment, the inhibitor of one or more RB-inactivating proteins is an inhibitor of a CDK protein, preferably an inhibitor of CDK4 and/or CDK6 (a "CDK4/6" inhibitor).

The amounts that are effective in combination means the amount of the CDK inhibitor, and the amount of the BCL2 inhibitor, which are effective in treating the disorders described herein when administered in combination. The amount of each therapeutic agent which is effective in combination may be equal to the amount which is effective when the therapeutic agent is administered on its own, or it may be less than the amount which is effective when the therapeutic agent is administered on its own (i.e. it may be a sub-optimal dose).

The combination therapy may be administered for a single fixed period of time, for example, 6 months, or 1, 2, or 3 or more years. The combination therapy may be administered according to a cyclical schedule, where there are alternating treatment and non-treatment periods. Alternatively, the combination therapy may be administered continuously. It is preferred that the combination therapy is administered continuously (until disease progression or unacceptable toxicity is reached).

In one embodiment, the CDK inhibitor and the BCL2 inhibitor are administered separately. When administered separately, the CDK inhibitor and the BCL2 inhibitor may be administered according to different dosing regimens and by different routes of administration. In another embodiment, the CDK inhibitor and the BCL2 inhibitor are administered sequentially. In this embodiment either therapeutic agent may be administered first. In yet another embodiment, the CDK inhibitor and the BCL2 inhibitor are administered simultaneously. In this embodiment, the agents may be administered in the same formulation or simultaneously via different routes of administration. The CDK inhibitor and the BCL2 inhibitor may be included in a single composition, or administered in separate compositions.

The CDK inhibitor and the BCL2 inhibitor may further be administered in combination with additional cancer treatment regimes, including, but not limited to, administration of radioactive isotopes, immunotherapies such as administration of anti-tumor antibodies, and administration of chemotherapeutic agents such as small molecule toxins, cytotoxic agents, or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE)A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes. Cancer treatment further includes removal of cancerous tissue or cells by surgery, biopsy, or other means. The CDK 4/6 inhibitor and the BCL2 inhibitor may further be administered in combination with additional lymphoma treatment regimes, including, but not limited to, chemotherapies such as CHOP (a combination including (i) cyclophosphamide such as cytoxan, (ii) doxorubicin or other topoisomerase II inhibitors such as adriamycin, (iii) vincristine or other vincas such as oncovin; and (iv) a steroid such as hydrocortisone or prednisolone); PI3K inhibitors such as Idelalisib/CAL-101/GS-1101 (Gilead Sciences); proteasome inhibitors such as velcade (Velcade bortezomib or PS341a); inhibitors of myc such as JQ1 (Filippakopoulos et al., *Nature* 468:1067-1073 (2010)); Bruton's tyrosine kinase (BTK) inhibitors such as ibrutinib (Pharmacyclics/Janssen Biotech); EZH2 (enhancer of zeste homolog 2) inhibitors such as El-1 (Novartis) or GSK126 (GlaxoSmithKline); and NFκB pathway inhibitors.

The CDK 4/6 inhibitor and the BCL2 inhibitor may further be administered in combination with antibodies such as Rituxan rituximab (anti-CD20), Zevalin Ibritumomab tiuxetan (Y90 anti-CD20), Bexxar tositumomab (1125 anti-CD20), Campath alemtuzumab (anti-CD52), and antibodies directed to CD19 or CD22; or with engineered immunoproteins such as chimeric antigen receptor expressing T cells (CARTS or CARETs), which are T cells engineered to express the antigen recognition domain of an antibody, which is linked to the signaling domain of the T cell receptor so that T-cells are activated upon binding of the tumor antigen by the antigen recognition domain.

BCL2 inhibitors include, but are not limited to:
ABT-737 with the structure:
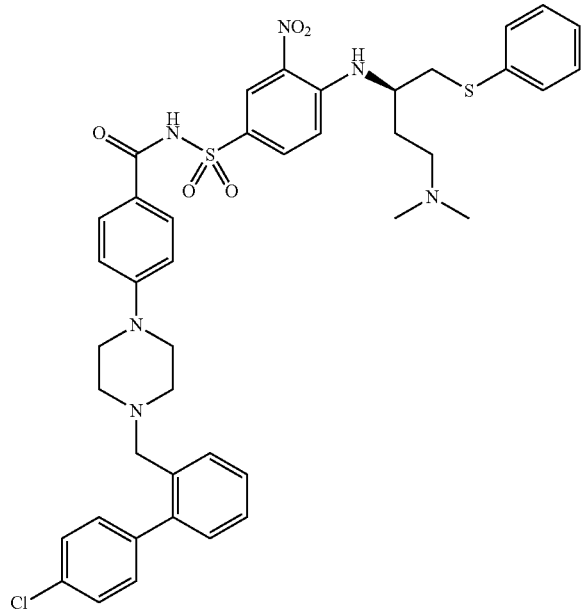 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]
Obatoclax mesylate (GX15-070) with the structure:
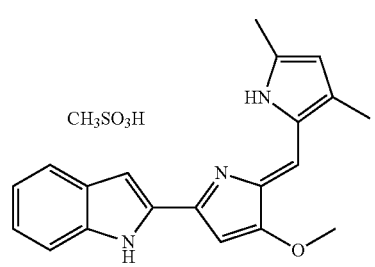 [SMILES: COC1=CC(c2cc3ccccc3[nH]2)=N/C1=C\c1[nH]c(C)cc1C ; "CH3SO3H"]
ABT-263 (Navitoclax) with the structure:
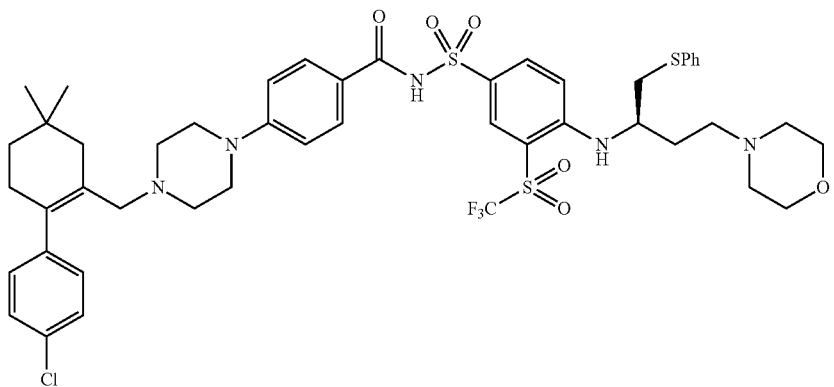
TW-37 with the structure:
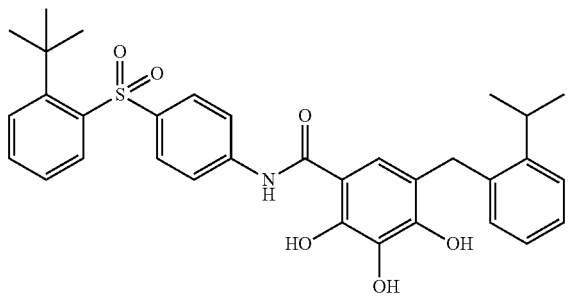 [SMILES: CC(C)c1ccccc1Cc1cc(C(=O)Nc2ccc(S(=O)(=O)c3ccccc3C(C)(C)C)cc2)c(O)c(O)c1O]
Exemplary CDK 4/6 inhibitors include, but are not limited to:
PD-0332991 (Pfizer) CDK4/6 inhibitor with the structure:
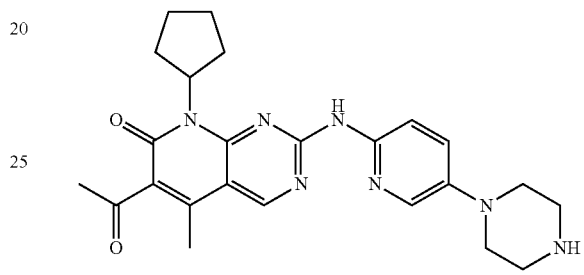
Flavopiridol CDK 1/2/4/6 inhibitor with the structure:
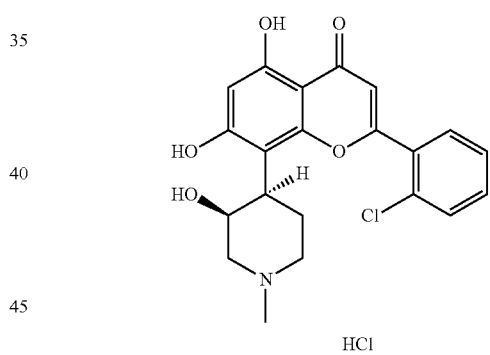

AT7519M (Astex Therapeutics) CDK 1/2/3/4/5/6 inhibitor with the structure:

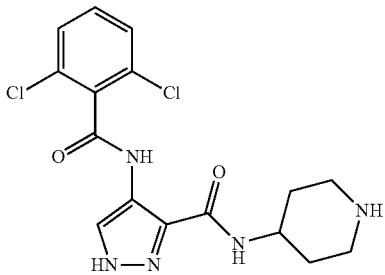 [SMILES: O=C(NC1CCNCC1)c1n[nH]cc1NC(=O)c1c(Cl)cccc1Cl]

P276-00 (Piramal Enterprises Limited) CDK1/4/9 inhibitor with the structure:

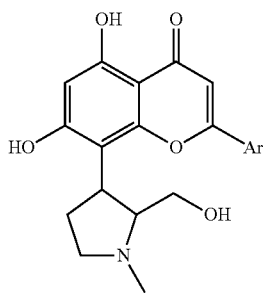

AG-024322 (Pfizer) CDK1/2/4 inhibitor with the structure:

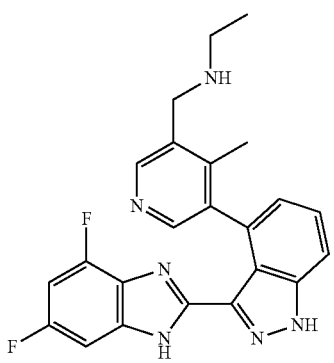 [SMILES: CCNCc1cncc(-c2cccc3[nH]nc(-c4nc5c(F)cc(F)cc5[nH]4)c23)c1C]

Additional CDK inhibitors include: LEE011 (Novartis) CDK4/6 inhibitor; LY2835219 (Lilly) CDK4/6 inhibitor; P1446A-05 (Piramal Enterprises Limited) CDK4 inhibitor; and BAY 1000394 (Bayer) CDK 1/2/3/4/7/9 inhibitor.

As used herein, "treatment" refers to clinical intervention in an attempt to alter the disease course of the individual or cell being treated, and can be performed either for prophylaxis or during the course of clinical pathology. Therapeutic effects of treatment include without limitation, preventing occurrence or recurrence of disease, alleviation of symptoms, diminishment of any direct or indirect pathological consequences of the disease, decreasing the rate of disease progression, amelioration or palliation of the disease state, and remission or improved prognosis. For example, treatment of a FL cancer patient may be reduction of tumor size, elimination of malignant cells, prevention of metastasis, or the prevention of relapse in a patient whose tumor has regressed.

As used herein, the terms "therapeutically effective amount" and "effective amount" are used interchangeably to refer to an amount of a composition of the invention that is sufficient to result in the prevention of the development, recurrence, or onset of cancer and one or more symptoms thereof, to enhance or improve the prophylactic effect(s) of another therapy, reduce the severity and duration of cancer, ameliorate one or more symptoms of cancer, prevent the advancement of cancer, cause regression of cancer, and/or enhance or improve the therapeutic effect(s) of additional anticancer treatment(s).

A therapeutically effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

For example, an "effective" therapy is able to achieve one, two or three or more of the following results, while an "ineffective" therapy achieves none of the following results: (1) an amelioration of cancer-related symptoms and/or quality of life; (2) a reduction or elimination in the cancer cell population; (3) a reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) the size of the tumor is maintained and does not increase or increases by less than 10%, or less than 5%, or less than 4%, or less than 2%, (10) an increase in the number of patients in remission, (11) an increase in the length or duration of remission, (12) a decrease in the recurrence rate of cancer, (13) an increase in the time to recurrence of cancer, or (14) a reduction in drug resistance of the cancer cells.

Aqueous compositions of the present invention comprise an effective amount of the combination of a BCL2 inhibitor and CDK inhibitor, preferably a combination of a BCL2 inhibitor and a CDK 4/6 inhibitor, further dispersed in a pharmaceutically acceptable carrier or aqueous medium.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

Administration may be by orthotopic, intradermal subcutaneous, intramuscular, intraperitoneal or intravenous injection. The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such excipients as, for example, pharmaceutical grades of mannitol, lactose, starch, magnesium stearate, sodium saccharine, cellulose, magnesium carbonate and the like. The compositions can take the form of solutions, suspensions, tablets, pills, capsules, sustained release formulations or powders.

The present disclosure is further illustrated by the following non-limiting examples.

EXAMPLES

Tumor ascertainment. Newly diagnosed FLs collected at Memorial Sloan-Kettering Cancer Center (MSKCC) since 1985 and evaluated by 3 haematopathologists, classified according to WHO criteria, were selected based on diagnosis and presence of an abnormal karyotype.

Array-CGH. DNA from fresh frozen or OCT (optical cutting temperature) media-embedded tissue was analyzed on an Agilent 244K oligonucleotide array and compared to human male DNA obtained from Promega (Cat# G147A) as a reference. All genomic positions described refer to UCSC May 2004 human reference sequence (hg17/NCBI build 35). The modified CBS algorithm was used to identify segmental gains and losses along the autosomes.

Immunohistochemical and TMA Methods. Tissue microarrays were constructed as previously published (Schatz et al., *J Exp Med* 208:1799-1807 (2011)), however, using a fully automated Beecher Instrument, ATA-27. The study cohort comprised of follicular lymphoma, consecutively ascertained at the Memorial Sloan-Kettering Cancer Center (MSKCC) between 1985 and 2000.

Sequencing and PCR amplification. The exonic regions of interest (NCBI Human Genome Build 36.1) were broken into amplicons of 350 bp or less, and specific primers were designed using Primer 3, to cover the exonic regions plus at least 50 bp of intronic sequences on both sides of intron-exon junctions. (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386). M13 tails were added to facilitate Sanger sequencing. PCR reactions were carried out in 384 well plates, in a Duncan DT-24 water bath thermal cycler, with 10 ng of template DNA (Repli-G Midi, Qiagen, Valencia, Calif.) as template, using a touchdown PCR protocol with Kapa2G Fast HotStart Taq (Kapa Biosystems, Cape Town, South Africa). The touchdown PCR method consisted of: 1 cycle of 95° C. for 5 min; 3 cycles of 95° C. for 30 sec, 64° C. for 15 sec, 72° C. for 30 sec; 3 cycles of 95° C. for 30 sec, 62° C. for 15 sec, 72° C. for 30 sec; 3 cycles of 95° C. for 30 sec, 60° C. for 15 sec, 72° C. for 30 sec; 37 cycles of 95° C. for 30 sec, 58° C. for 15 sec, 72° C. for 30 sec; 1 cycle of 70° C. for 5 min. Templates were purified using AMPure (Beckman Coulter Genomics, Beverly, Mass.). The purified PCR reactions were split into two, and sequenced bidirectionally with M13 forward and reverse primer and Big Dye Terminator Kit v.3.1 (Applied Biosystems, Foster City, Calif.), at Beckman Coulter Gernomics. Dye terminators were removed using the CleanSEQ kit (Beckman Coulter Gernomics), and sequence reactions were run on ABI PRISM 3730xl sequencing apparatus (Applied Biosystems, Foster City, Calif.).

Mutation detection. Mutations were detected using an automated detection pipeline at the Memorial Sloan-Kettering Cancer Center (MSKCC) Bioinformatics Core. Bi-directional reads and mapping tables (to link read names to sample identifiers, gene names, read direction, and amplicon) were subjected to a QC filter which excludes reads that have an average phred score of <10 for bases 100-200. Passing reads were assembled against the reference sequences for each gene, containing all coding and UTR exons including 5 Kb upstream and downstream of the gene, using command line Consed 16.0 (PMID: 9521923). Assemblies were passed on to Polyphred 6.02b (PMID: 9207020), which generated a list of putative candidate mutations, and to Polyscan 3.0 (PMID: 17416743), which generated a second list of putative mutations. The lists were merged together into a combined report, and the putative mutation calls were normalized to '+' genomic coordinates and annotated using the Genomic Mutation Consequence Calculator (PMID: 17599934). The resulting list of annotated putative mutations was loaded into a Postgres database along with select assembly details for each mutation call (assembly position, coverage, and methods supporting mutation call). To reduce the number of false positives generated by the mutation detection software packages, only point mutations which are supported by at least one bi-directional read pair and at least one sample mutation called by Polyphred were considered, and only the putative mutations which are annotated as having non-synonymous coding effects, occur within 11 bp of an exon boundary, or have a conservation score>0.699 were included in the final candidate list. Indels called by any method were manually reviewed and included in the candidate list if found to hit an exon. All putative mutations were confirmed by a second PCR and sequencing reaction, in parallel with amplification and sequencing of matched normal tissue DNA. All traces for mutation calls were manually reviewed.

Copy Number analysis. All genomic positions described in this study refer to UCSC May 2004 human reference sequence (hg18/NCBI build 36). A modified CBS algorithm was used to initially identify segmental gains and losses along the autosomes. To estimate the frequency of copy number changes for each gene, log 2 ratio signals from the CBS output were converted into discrete copy number calls (loss=−1, diploid=0, gain=1) defining the status of each gene in each sample. Gains and losses were determined using a sample-specific threshold based on 2.22 median absolute deviations (approximately corresponding to 1.5 standard deviations) from the residual between probe-level data and means of segments having uniform DNA copy number level. Putative homozygous deletions are defined for probe level below −2*Ts.

Gene peaks of amplification and deletions analysis. For each region of common copy number change, gene peaks were extracted as follow: 1) Define a discrete function F such that F(g) is the frequency of alteration of gene g, and genes are ordered according to their genomic locus. 2) For each local maximum $F(g_{max})=F_{max}$ of F, select the minimal set of genes contiguous to $g_{max}$ such that their alteration frequency is $>k*F_{max}$ with $k \in (0,1)$. For this analysis the inventors used k=0.95. 3) Each selected gene set is a candidate gene peak. Iteratively, merge pairs of overlapping gene peaks, whereas each gene within the union of the two satisfies the frequency constraint at Step 2. The inventors included in this analysis all regions of copy number changes smaller than 5 MB occurring in at least 5% of the cases.

Mutually Exclusivity analysis. To identify significant mutually exclusive pattern of copy number alteration the inventors used the algorithm MEMo (Ciriello et al., *Genome Res* 22:398-406 (2012)). Briefly, MEMo used as input the set of gene peaks of gain and loss derived from the array-CGH analysis. Alterations targeting fully connected gene sets were tested for mutual exclusivity based on a random permutation of the observed genomic alterations. Genomic events were permuted using a Monte Carlo Markov Chain approach that preserved both the number of alterations per gene and the number of alterations per sample.

Clinical data analysis. Under Memorial Sloan-Kettering Cancer Center (MSKCC) IRB waiver approval, clinical information was analyzed from a collection of 62 FL cases. In the survival analysis were included patients<70 years old and last follow up before 2008. Statistical Methods: The association between the alteration in cell cycle genes (binary yes/no) and GRADE and FLIPI are compared using Fisher's Exact test. Overall survival is summarized using Kaplan-Meier curves and tests of association between the categorical variables (alteration, GRADE, FLIPI) and survival is conducted using the Prentice-Wilcoxon test which was chosen since the survival differences are more different in the earlier time points. The association between cell cycle alteration and survival was adjusted for an established prognostic factor FLIPI conducted using FLIPI as a stratification variable. All the analyses were conducted in R.

Gene Expression Array and analysis. Affymetrix U133A gene chips were used for gene expression profiling of 72 FL samples. The transcriptome analyses were performed using RMA system software packages (version 2.8.0) including Bioconductor (version 2.0). Raw gene expression data from Affimetrix CEL files were analyzed by using the affy R library from Bioconductor to generate probe level intensity. Gene centric expression values were generated using a CDF file based on remapping of probes to the human genome 36.1. The raw data for 72 FL patient samples (CEL file) and the normalized matrix have been deposited in Gene Expression Omnibus database (submitted).

Immunohistochemical and TMA Methods. Tissue microarrays were constructed as previously published (Schatz et al., *J Exp Med* 208:1799-1807 (2011)), however, using a fully automated Beecher Instrument, ATA-27. The study cohort comprised of follicular lymphoma, consecutively ascertained at the Memorial Sloan-Kettering Cancer Center (MSKCC) between 1985 and 2000. Use of tissue samples were approved with an Institutional Review Board Waiver and approval of the Human Biospecimen Utilization Committee. All cancer biopsies were evaluated at MSKCC, and the histological diagnosis was based on hematoxylin and eosin (H&E) staining. TMAs were stained with the P-Rb (Ser780) and Cyclin D3 antibody (Cell Signaling) 1:500, with anti-CDK4 (DCS-31; Invitrogen) 1:500 and stained for Ki67 in a Ventana Discovery XT automated biomarker platform stainer (Tuscon, Ariz.), using protocol 67: CC1, standard, at 1:100 dilution overnight at 4 C, then with a secondary anti-rabbit antibody from Vector Labs (Burlingame, Calif.), at 1:200 dilution for 60 min.

Fluorescence In Situ Hybridization. FISH was performed using BAC clones spanning CDK4 in 12q13: RP11-571M6 (part of a 1 Mb clone set kindly supplied by the Wellcome Trust Sanger Institute (Staudt, *N Engl J Med* 356:741-742 (2007))) and RP11-970A5 (from BACPAC resources, Children's Hospital at Oakland Research Center). The BACs were labeled by nick translation with Red-dUTP (Enzo Life Sciences, supplied by Abbott Molecular, Inc.), and hybridized with chromosome 12 centromeric repeat pα12H8, labeled with Orange-dUTP, as reference. The baseline autofluorescence of many tumor cores was quite high, and the orange dye was used instead of the more usual Green-dUTP in an attempt to improve probe visibility. The tissue microarray slides were hybridized according to standard procedures. Briefly, the slides were de-waxed, microwaved in 10 mM sodium citrate buffer pH6.0, and treated with pepsin-HCl. Slides with probe mix were co-denatured on a HYBrite automated hybridizing station (Abbott Molecular Inc.) at 80° C. for 8 minutes, then incubated for 2-3 days at 37° C. After coverslip removal the slides were washed using standard non-formamide stringency washes, stained with DAPI, then mounted in antifade solution (Vectashield, Vector Labs). The slides were scanned at low resolution using a Metafer MetaCyte automated scanning system (Metasystems Group Inc, Waltham, Mass.), comprising a Zeiss Axioplan 2i epifluorescence microscope equipped with a megapixel CCD camera (CV-M4+CL, JAI), and motorized stage (Martzhauser). The scanned image was then segmented into individual cores using the MetaCyte TMA tool and high-resolution compressed image z-stacks (9×0.5 um) were captured using Isis 5.2 FISH imaging software. Orange signals were pseudo-colored in green for clarity, and CDK4 and reference signals were counted for each image and the ratio calculated for each core.

Generation of mice. The vavP Bcl2 mouse model of FL (Lowe et al., *Nature* 432:307-315 (2004)) was adapted to adoptive transfer of retrovirally transduced HPCs[1]. Data were analyzed in Kaplan-Meier format using the log-rank (Mantel-Cox) test for statistical significance. H&E, Ki67, TUNEL, P-RB, and surface marker analysis were as in (Staudt, *N Engl J Med* 356:741-742 (2007)).

Xenografts and treatment studies. Xenograft mice were generated as described (Schatz et al., *J Exp Med* 208:1799-1807 (2011)); briefly, s.c. injection of 5 Mio DoHH2 or SU-DHL-8 human lymphoma cells mixed with matrigel (BD Bioscience, 354230) into the flanks of NOD/SCID (NOD.CB17-Prkdc$^{scid}$/J) mice. Upon reaching a tumor size of 100 mm$^3$ mice were treated daily by gavage with 150 mg/kg with PD-0332991 (Chemitek CT-PD2991) diluted in 50 mmol/L sodium lactate (pH4) for 2 weeks and with ABT-737 50 mg/Kg dilute in PTD solution (30% propylene glycol, 5% Tween 80 65% D5W) for 2 weeks and Obatoclax 2 mg/kg intra-venous diluted in 5% of Dextrose in water solution for 1 week. The control animals were treated with 50 mmol/L sodium lactate (pH4), PTD solution and 5% of Dextrose in water solution respectively. Tumors were weighed and volumes were measured twice weekly.

Cell culture, cell cycle and viability assays. Lymphoma cell lines DoHH2, Ly-8, Su-DHL-6, Su-DHL-16, Su-DHL-8 and Su-DHL-10 were maintained in RPMI 1640 with 10% fetal bovine serum, 1% L-Glutamine and 1% penicillin/streptomycin. Human lymphoma cell lines treated with PD-0332991 and Obatoclax were analyzed for cell viability and cell cycle assays. Briefly, cells were seed at 5×10^5 per mL and they were treated with PD-0332991 and/or ABT-737 and/or Obatoclax. After 24 h of treatment cell viability was assessed using CellTiter-Glo reagent (Promega). Cell cycle assay based on uptake of DNA staining dye using Cell Cycle Reagent assays (cat. 4700-0169 from Guava Technologies, Millipore) was performed following to manufacturer instructions. The culture of IL-7 dependent B-cells was as described in (Pasqualucci et al., Nature genetics 43:830-837 (2011)).

Western blot analysis. Immunoblots were performed from whole cell lysates or tissue samples as described (Steidl et al., Nature 471:377-381 (2011)). Briefly, 30 µg of protein/sample were resolved on SDS-PAGE gels and transferred to Immobilon-P-membranes (Millipore). Antibodies were against Rb (Cell Signaling cat #9309), Phospho-Rb S780 (Cell Signaling cat #3590), Phospho-Rb S795 (Cell Signaling cat #7986), CDK4 (Cell Signaling cat #2906), CyclinD3 (Cell Signaling cat #2936), Cyclin D1 (Cell Signaling cat #2926), Cyclin D2 (Cell Signaling cat #2924) p16 (Santa Cruz Biotechnology cat # sc 1207), Caspase 3 (Cell Signaling cat #9662) Tubulin (1:5000; Sigma, B-5-1-2). Enhanced chemiluminescence was used for detection (ECL, Amersham).

Cell cycle controls are common mutational targets in aggressive B-cell malignancies (Schmitz et al., Nature, (2012), Monti et al., Cancer Cell 22:359-372 (2012)), by contrast only individual reports find aberrations in FL (Chim et al., Human pathology 38:1849-1857, (2007), Alhejaily et al., Human pathology 42:972-982 (2011), Pruneri et al., International journal of cancer. Journal international du cancer 112:71-77 (2004)) and their role in FL pathogenesis and treatment is unclear. By sequencing 69 FL samples we identify recurrent mutations in the CCND3 PEST domain in 6% of FLs. CYCLIND3 is the only D-type CYCLIN that is significantly expressed in FL (Gene Expression Omnibus Access. #GSE37088) (FIG. 5A). The mutations cluster in the PEST domain and are typically heterozygous with only one case harboring a homozygous T283A mutation (#107-2124) (FIGS. 1A/B). Similar mutations in the CYCLIND3 PEST domain occur in aggressive lymphomas and other cancers (Pasqualucci et al., Nature genetics 43:830-837 (2011), Morin et al., Nature 476:298-303 (2011), Morin et al., Nat Genet 42:181-185 (2010), Musgrove et al., Nat Rev Cancer 11:558-572 (2011)). (FIG. 5B). These mutations increase the stability of the CYCLIN D3 protein, e.g. the T283A mutation affects a phosphorylation site that is required for proteasomal degradation (Naderi et al., Journal of cell science 117:3769-3783 (2004)). Accordingly, cycloheximide treatment of 293T and immortalized B-cells engineered to express mutant and wild type CYCLIN D3 confirms increased stability of the mutant CYCLIN D3 proteins (T283A, V287D, and Q276*) (FIG. 5C/E).

To explore whether cell cycle control loci are more broadly involved in FL, the inventors analyzed 64 FL samples by array-comparative hybridization (aCGH). The inventors focused on focal (<5 MB) and recurrent (>5%) chromosomal lesions. Within wider altered regions the inventors defined peaks of regional gains and losses by selecting the most frequently altered gene in each region and included adjacent genes whose alteration frequency was at least 95%. Physiological changes and copy number variations were excluded as described (Oricchio et al., Cell 147:554-564 (2011)). This analysis identified 43 gene peaks including 25 regions of gain and 18 regions of genomic loss in FL (FIG. 1C). The most frequently amplified peak (31% of cases) affected chromosome 12 and one of the most frequently altered genes in this peak was CDK4. In addition, highly focal losses affected the CDKN2a/b locus at chromosome 9p21.3 (5 cases, 9%, 1 homozygous loss) and the RB locus at chromosome 13q14 (6 cases, 10%) (FIG. 1C, FIG. 6). Quantitative RT-PCR confirmed corresponding changes in the expression of CDK4, p16 and RB (FIG. 6C/F/I). Moreover, a genome-wide and unbiased analysis of the interrelation between chromosomal changes (Mutual Exclusivity Modules analysis—MEMo) (Ciriello et al., Genome Res 22:398-406 (2012)) revealed mutually exclusive relations between these specific regions of chromosomal change in FL (p-value<0.01, FDR corrected p-value<0.1) (FIG. 1D). The gain of function mutations in CCND3 co-occur with gains in CDK4 in 2 of 4 cases (not shown), perhaps consistent with a co-requirement for increased CDK levels. While each genomic lesion affects other genes as well, their mutual exclusive genetic relation together with the known functional relationship (Musgrove et al., Nat Rev Cancer 11:558-572 (2011)) indicates that these cell cycle regulators are important targets of aberrations in FL.

Next the inventors examined these genomic findings in a larger patient cohort using tissue micro arrays (TMAs). First, 46% of FLs showed abundant RB phosphorylation (Ser 780) (FIG. 2A, FIG. 7D). This corresponds to the frequency of genetic lesions that activate CDK4 in FL (FIG. 1). FISH analysis confirmed gains of CDK4 in 22 of 80 cases (27.5%) (FIG. 7A), and the inventors find abundant CDK4 expression in 73 of 106 (69%) of FL cases including most (11/13) cases with chromosomal gains (FIG. 2B, FIG. 7B). Consistent with the RNA data (FIG. 5A), the inventors confirm abundant CYCLIN D3 expression in 74 of 104 cases (71%) (FIG. 7C). As expected, most tumors with chromosomal gains or high protein levels of CDK4 and CYCLIN D3 were also positive for phosphorylated RB (FIG. 7E). Hence, protein studies confirm functional inactivation of RB by increased CDK4/CYCLIN D3 activity in a significant subset of human FL.

Next, the inventors explored the clinical impact of cell cycle activating lesions in FL. The inventors found the mean survival of patients whose tumors showed copy number changes affecting CDK4, CDNK2a, or RB was 5.1 years shorter than patients whose tumors were diploid at these loci (median survival: 9.8 years versus 4.7 years, p=0.052) (FIG. 2C). FL prognosis is estimated by the standardized Follicular Lymphoma International Prognostic Index (FLIPI) that reflects parameters of disease spread (e.g. stage, number of involved lymph nodes, serum lactate dehydrogenase (LDH), hemoglobin) and patient age (Federico et al., J Clin Oncol 27: 4555-4562 (2009), Solal-Celigny et al., Blood 104:1258-1265 (2004)). In the cohort 45% of patients were low risk by FLIPI, 26% intermediate, and 29% high-risk. Overall, this distribution resembles the risk distribution reported in other cohorts (Solal-Celigny et al., Blood 104:1258-1265 (2004), Arcaini et al., Leukemia & lymphoma 47:1018-1022 (2006)). As expected FLIPI was associated with outcome of standard therapy (FIG. 2D). Moreover, genomic lesions at cell cycle loci were significantly associated with high risk by FLIPI (p=0.002), such that most high-risk tumors by FLIPI had cell cycle activating lesions (13/17) (FIG. 2D). Ki67 staining revealed that 21% of tumors were strongly positive of Ki67 (>50% positive cells) (FIG. 2E). As expected tumors with genomic lesions in cell cycle loci or CCND3 mutation were typically in this proliferative category enriched in the high-risk group defined by FLIPI. Histological grade considers the ratio of centroblasts to centrocytes in biopsy samples and is not considered a solid prognostic indicator (His et al., Archives of pathology & laboratory medicine 128:863-868 (2004), Martin et al., Blood 85:3671-3678 (1995), Hans et al., Blood 101:2363-2367 (2003)). Accordingly, in the cohort grade alone did not reflect outcome (p=0.74) (FIG. 8A). Moreover, genomic lesions affecting cell cycle loci occurred across all tumor grades and were not associated with increased grade (p=0.9) (FIG. 8B). The inventors noticed however that expression of cell cycle genes was elevated in high-grade tumors and this likely reflects the higher ratio of proliferative centroblasts with advanced tumor grade (Klein et al., *Nat Rev Immunol* 8:22-33 (2008)) (FIG. 8C/D). Hence, genomic lesions in cell cycle loci identify a high-risk population of FL patients who may benefit from specific, cell cycle directed therapies.

Next, the inventors examined the role of cell cycle deregulation in FL pathogenesis. The murine model recapitulates key aspects of the genetics and morphology of FL and is based on the adoptive transfer of vav-P-Bcl2 hematopoietic progenitor cells (HPCs) (Ciriello et al., *Genome Res* 22:398-406 (2012), Egle et al., *Blood* 103:2276-2283 (2004)). (FIG. 3A). Briefly, the inventors transduced vavPBcl2 HPCs with MSCV constructs directing the expression of CDK4, a kinase dead mutant form of CDK4 (CDK4 KD), mutant CYCLIN D3 (T283A), or c-MYC, and short-hairpin RNAs (shRNAs) targeting p16 or RB. Mice receiving HPCs over-expressing CDK4 or mutant CYCLIN D3 developed tumors with high incidence and short latency compared to vector or CDK4 KD although not as rapidly as c-MYC transduced HPCs (CDK4: n=11, median latency 58 days p(CDK4 vs vector=0.001; CYCLIN D3 T283A: n=10, median latency 87 days p(CYCLIN D3 T283A vs vector=0.05); Vector controls: n=24, 80% tumor free, CDK4 KD, n=10, 100% tumor free; p(Cdk4 vs. vector)=0.001; c-Myc: n=7) (FIG. 3B). Similarly, knock down of p16 (n=11, median latency 70 days, p(shp16 vs. vector=0.018) and knockdown of RB (n=9, median latency 70 days; p(shRb vs. vector)<0.01) strongly cooperated with Bcl2 in FL development (FIG. 3B). The kinase activity of CDK4 was also required in an in vitro assay for B-cell proliferation, and shRNAs against Dleu2, a non-coding RNA close to the RB locus, did not enhance B-cell fitness in vitro (FIG. 9). Surface marker analysis confirmed the B-cell lymphoma with varying degrees of T-cell infiltration. c-MYC expressing tumors resembled transformed FLs and were composed of large cells, with loss of PNA staining and a diffuse growth patterns. Lymphomas harboring cell cycle lesions were composed of smaller B-cells and maintained variable degrees of follicular organization best seen in the PNA stain (FIG. 3C). Consistent with the human TMA data, these tumors had higher levels of phosphorylated Rb and were more proliferative by Ki67 with individual mitotic Fig.s (FIG. 3C). Hence, cell cycle activation is an oncogenic driver and cooperates with Bcl2 in a murine FL model.

PD-0332991 is a novel and highly selective CDK4/6 inhibitor that is currently in early clinical trials against several cancers (Fry et al., *Mol Cancer Ther* 3:1427-1438 (2004), Flaherty et al., *Clin Cancer Res* 18:568-576 (2012)). Most FL cell lines are derived from transformed FLs and are carry the hallmark translocation t(14;18). These include DoHH2, Su-DHL-6, Su-DHL-16 and Ly 8 cells. These lines also have high levels of CDK4, CDK6, and phosphorylated RB (S780 and S795) (FIG. 10A) and DoHH2 cells carry a homozygous p16 deletion (Gronbaek et al., *Leukemia* 14:1727-1735 (2000)). To examine the effect of targeted therapies, the inventors first treated DoHH2, Su-DHL6, Su-DHL-16, and Ly8 cells with increasing doses of PD-0332991. In all lines PD-0332991 caused complete growth arrest and accumulation in the G1 phase with loss of RB phosphorylation (FIG. 4B/C, FIG. 10C-H) The cytostatic effect of PD-0332991 required RB and knockdown of RB bypassed the cell cycle arrest in DoHH2 (FIG. 4D/E). Further, knockdown of either CDK4 or CDK6 alone was not sufficient for cell cycle arrest indicating functional compensation between these homologous RB kinases and the requirement to block both (FIG. 10I/J). Given the limitations of transformed FL-derived lines, the inventors also tested PD-0332991 against primary murine vavBcl2 induced lymphomas in vivo. Here, PD-0332991 induced responses in vavBcl2/CDK4 lymphoma bearing animals, but was ineffective against histologically transformed vavBcl2/c-MYC lymphomas (FIG. 10K). Hence, pharmacological inhibition of the CDK4/6 kinases restores RB function and growth control across several human FL-derived lines and in primary, non-transformed murine FLs.

The translocation t(14;18) is the cytogenetic hallmark of FL and promotes lymphoma cell survival by activating the anti-apoptotic BCL2 protein. BH3 mimetic drugs like ABT-737 block BCL2 function by inserting into the BH3-binding groove of anti-apoptotic BCL2 proteins (Oltersdorf et al., *Nature* 435:677-681 (2005)). Accordingly, ABT-737 has selective activity against cell lines that carry the translocation t(14;18) and powerfully induced apoptosis and caspase cleavage in these FL-derived cell lines (e.g. DoHH2, Su-DHL-6, Su-DHL-16, Ly8) (FIG. 4F/G, FIG. 11A). This pro-apoptotic in vitro activity was further enhanced by concomitant treatment with PD-0332991 in both DoHH2 and Su-DHL-6 cells (p<0.001) (FIG. 4F). The inventors observed this additive drug interaction in vivo against FL xenografts and primary murine FLs. Briefly, xenografted DoHH2 cells were treated when tumors were fully established (>10 mm3) with PD-0332991 (PD: 150 mg/kg, alternate days p.o., days 1-14) or ABT-737 (ABT: 50 mg/kg, alternate days, i.v., day 1-14) somewhat restrained tumor growth during the treatment course, but residual tumors rapidly expanded thereafter. By contrast, combining both drugs (PD: 150 mg/kg; ABT: 50 mg/kg, on alternate day 1-14) completely abrogated growth and caused lasting and complete (decrease by >95-100%) responses (PD+ABT vs. PD or ABT)<0.004) (FIG. 4H/I). As expected, PD-0332991 caused complete loss of RB phosphorylation (Ser 780) and slowed proliferation by Ki67 in vivo (FIG. 4J/L). ABT-737 produced significant cell death indicated by caspase cleavage and TUNEL stains (FIG. 4K/L). Together, the drugs caused both loss of proliferation (Ki67) and extensive cell death in histological analyses (FIG. 4L). Similarly, the combination of PD-0332991 and ABT-737 was highly effective against primary murine tumors (FIG. 11B) and decreased disease burden in animals transplanted with vavBcl2 tumor cells in a manner superior to PD-0332991 treatment alone (FIG. 10K).

The inventors confirmed results with a second BH3 mimetic Obatoclax (OBX). Briefly, Obatoclax was less selective for cells carrying the translocation t(14;18) indicating a broader spectrum than ABT-737 (FIG. 10A). Single agent OBX potently induced cell death in vitro and this was further enhanced by PD-0332991 (FIG. 10B/C). As seen with ABT-737, OBX also enhanced xenograft responses to PD-0332991 in vivo and induced both cell death by TUNEL and growth arrest in xenografted FL cells (FIG. 10D-G). These results indicate that combined CDK4/6 and BCL2 blockade can produce powerful therapeutic responses in murine and xenograft models of FL.

Next, the inventors examined in detail the potential toxicity of this combination treatment. Briefly, the inventors saw no pathologic changes in organ histologies, or drop in body weight. Serum chemistry was unchanged, and the main toxicity was a drop in white cell numbers that reflected single agent and combination effects on lymphocytes and a temporary reduction in platelet counts (FIG. 11).

Hence, dual blockade of CDK4 and BCL2 is a feasible and highly effective combination therapy for high risk FL with low toxicity

What is claimed is:

1. A pharmaceutical composition for treating follicular lymphoma, comprising a combination of a sub-optimal dose of a B-cell lymphoma-2 (BCL2) inhibitor selected from ABT-737 or Obatoclax mesvlate, and a sub-optimal dose of the cyclin-dependent kinase (CDK) inhibitor PD-0332991, wherein the combination is effective for the treatment of a patient identified as having retinoblastoma (RB)-inactivated FL.

2. A method of treating follicular lymphoma (FL) in a patient identified as having retinoblastoma (RB)-inactivated FL, comprising administering a combination of a sub-optimal dose of a B-cell lymphoma-2 (BCL2) inhibitor selected from ABT-737 or Obatoclax mesylate, and a sub-optimal dose of the cyclin-dependent kinase (CDK)4/6 inhibitor PD-0332991, in an amount effective to treat RB-inactivated FL in said patient.

3. The method of claim 2, wherein the patient has been identified as having retinoblastoma (RB)-inactivated FL by detecting a biomarker associated with inactivation of the retinoblastoma (RB) protein in a sample from said patient.

4. The method of claim 3, wherein said biomarker is selected from one or more of the group consisting of phosphorylated RB protein, increased level or activity of cyclin-dependent kinase (CDK)4, increased level or activity of Cyclin D3, and decreased level or activity of p16.

5. The method of claim 3, wherein said biomarker is a genetic alteration in one or more of the Rb locus, the CDK4 locus, the Cyclin D3 locus, or the CDKN2A/B locus.

6. A pharmaceutical composition for treating follicular lymphoma, comprising a combination of a B-cell lymphoma-2 (BCL2) inhibitor selected from ABT-737 or Obatoclax mesylate, and the cyclin-dependent kinase (CDK) inhibitor PD-0332991, wherein the combination is effective for the treatment of a patient identified as having retinoblastoma (RB)-inactivated FL.

7. A method of treating follicular lymphoma (FL) in a patient identified as having retinoblastoma (RB)-inactivated FL, comprising administering a combination of a B-cell lymphoma-2 (BCL2) inhibitor selected from ABT-737 or Obatoclax mesylate, and the cyclin-dependent kinase (CDK)4/6 inhibitor PD-0332991, in an amount effective to treat RB-inactivated FL in said patient.

8. The method of claim 7, wherein the patient has been identified as having retinoblastoma (RB)-inactivated FL by detecting a biomarker associated with inactivation of the retinoblastoma (RB) protein in a sample from said patient.

9. The method of claim 8, wherein said biomarker is selected from one or more of the group consisting of phosphorylated RB protein, increased level or activity of cyclin-dependent kinase (CDK)4, increased level or activity of Cyclin D3, and decreased level or activity of p16.

10. The method of claim 8, wherein said biomarker is a genetic alteration in one or more of the Rb locus, the CDK4 locus, the Cyclin D3 locus, or the CDKN2A/B locus.

* * * * *